US012423886B2

(12) United States Patent
Firsching et al.

(10) Patent No.: US 12,423,886 B2
(45) Date of Patent: Sep. 23, 2025

(54) PROCESSING DEVICE FOR OBTAINING GAP FILLER SINOGRAM INFORMATION, COMPUTER TOMOGRAPH, METHOD AND COMPUTER PROGRAM

(71) Applicant: Fraunhofer-Gesellschaft zur Foerderung der angewandten Forschung e.V., Munich (DE)

(72) Inventors: Markus Firsching, Erlangen (DE); Alexander Ennen, Erlangen (DE); Christoph Speier, Erlangen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 492 days.

(21) Appl. No.: 17/691,913

(22) Filed: Mar. 10, 2022

(65) Prior Publication Data

US 2022/0292743 A1    Sep. 15, 2022

(30) Foreign Application Priority Data

Mar. 12, 2021    (EP) .................................... 21162349

(51) Int. Cl.
*G06T 11/00* (2006.01)
*A61B 6/00* (2006.01)
(Continued)

(52) U.S. Cl.
CPC .............. *G06T 11/008* (2013.01); *A61B 6/03* (2013.01); *A61B 6/482* (2013.01); *A61B 6/5217* (2013.01);
(Continued)

(58) Field of Classification Search
None
See application file for complete search history.

(56) References Cited

U.S. PATENT DOCUMENTS

2004/0267114 A1*  12/2004  Mundy .................. A61B 6/032
                                                600/427
2018/0182129 A1*   6/2018  Xing ..................... G06T 7/0012
(Continued)

FOREIGN PATENT DOCUMENTS

JP       2009082250 A       4/2009
JP       2020096693 A  *    6/2020   ............. A61B 6/032
(Continued)

OTHER PUBLICATIONS

Alvarez, R.E., et al., "Energy-selective reconstructions in X-ray computerised tomography", Physics in Medicine & Biology, 21(5), 733., 13 pp.
(Continued)

*Primary Examiner* — Akwasi M Sarpong
*Assistant Examiner* — Pawan Dhingra
(74) *Attorney, Agent, or Firm* — Perkins Coie LLP; Michael A. Glenn

(57) ABSTRACT

A processing device for obtaining gap-filler sinogram information is adapted to obtain first sinogram information associated with a first spectral parameter, and second sinogram information associated with a second spectral parameter, and is adapted to obtain the gap-filler sinogram information which is associated with the second spectral parameter and which fills the one gap in the second sinogram information, on the basis of the first sinogram information and the second sinogram information. A computer program, a method, and a computer implementation are also described.

20 Claims, 9 Drawing Sheets

(51) Int. Cl.
    A61B 6/03    (2006.01)
    G06T 7/00    (2017.01)
    G06T 7/30    (2017.01)
(52) U.S. Cl.
    CPC .............. *G06T 7/0012* (2013.01); *G06T 7/30*
        (2017.01); *A61B 6/542* (2013.01); *G06T*
        *2207/20084* (2013.01); *G06T 2207/30004*
        (2013.01); *G06T 2211/408* (2013.01)

(56) References Cited

U.S. PATENT DOCUMENTS

2020/0193655 A1*  6/2020  Taguchi ............... G06T 11/005
2020/0196972 A1*  6/2020  Zhou .................... A61B 6/4014
2021/0007691 A1*  1/2021  Prabhu Verleker .... A61B 6/405

FOREIGN PATENT DOCUMENTS

JP    2020099662 A    7/2020
JP    2021010623 A    2/2021
JP    2021010727 A    2/2021
WO    2014115625 A1   7/2014
WO    2016017534 A1   2/2016

OTHER PUBLICATIONS

Cao, Wenchao, et al., "GAN-based sinogram completion for slow triple kVp switching CT", Progress in Biomedical Optics and Imaging, SPIE- International Society for Optical Engineering, Bellingham, WA, US, Bd. 11595, Feb. 15, 2021 (Feb. 15,2021), pp. 1159520-1159520, XP060139633, 7 pp.

Cao, Wenchao, et al., "Slow triple kVp switching CT with convolutional neural network based sinogram completion and material decomposition", The 6th International Conference On Image Formation in X-Ray Computed Tomography, Aug. 3, 2020 (Aug. 3, 2020), XP05582838, 4 pp.

Clark, Darin P., et al., "Deep learning based spectral extrapolation for udal-source, dual-energy x-ray computed tomography", Medical Physics., 2020, 16 pp.

Coleman, A.J., et al., "A beam-hardening correction using dual-energy computed tomography", Physics in Medicine & Biology, 30(11), 1251, 7 pp.

Dremel, Kilian, et al., "Beam Hardening Correction in X-Ray Computed Tomography: A Comparison of Two Iterative Model-Based Reconstruction Methods", 11th European Conf. Non-Destructive Testing (Prague, Czech Republic,)., 10 pp.

Feldkamp, L.A., et al., "Practical cone-beam algorithm", (1984) 612 J. Opt. Soc. Am. A/vol. 1, No. 6, 8 pp.

Ghani, Muhammad Usman, et al., "Deep Learning-Based Sinogram Completion for Low-Dose CT", In 2018 IEEE 13th Image, Video, and Multidimensional Signal Processing Workshop (IVMSP) (pp. 1-5). IEEE., Jun. 2018, 5 pp.

Herman, Gabor T., "[Uploaded in 11 parts] Fundamentals of Computerized Tomography: Image Reconstruction from Projections", Advances in Pattern Recognition. Second Edition. Springer Science & Business Media. 2009, 2009, 18 pp.

Johnson, Thorsten R.C., et al., "Material differentiation by dual energy CT: initial experience", European radiology, 17(6), 1510-1517, (2007)., Oct. 20, 2006, 9 pp.

Kuchenbecker, Stefan, et al., "Dual energy CT: How well can pseudo-monochromatic imaging reduce metal artifacts?", Medical physics, 42(2), 1023-1036., 16 pp.

Li, Ziheng, et al., "A Sinogram Inpainting Method based on Generative Adversarial Network for Limited-angle Computed Tomography", In 15th International Meeting on Fully Three-Dimensional Image Reconstruction in Radiology and Nuclear Medicine (vol. 11072, p. 1107220). International Society for Optics and Photonics., 5 pp.

Mathews, John D., et al., "Cancer risk in 680 000 people exposed to computed tomography scans in chilhood or adolescence: data linkage study of 11 million Australians", BMJ 2013; 346., May 22, 2013, 18 pp.

Patino, Manuerl, et al., "Material Separation Using Dual-Energy CT: Current and Emerging Applications", Radiographics, 36(4), 1087-1105., 19 pp.

Poirot, Maarten G., et al., "Physics-informed Deep Learning for Dual-Energy Computed Tomography Image Processing", Scientific reports, 9(1), 1-9., 2019, 9 pp.

Ronneberger, Olaf, et al., "U-Net: Convolutional Networks for Biomedical Image Segmentation", In International Conference on Medical image computing and computer-assisted intervention (pp. 234-241). Springer, Cham, 8 pp.

Thaler, Franz, et al., "Sparse-View CT Reconstruction Using Wasserstein GANs", In International Workshop on Machine Learning for Medical Image Reconstruction (pp. 75-82). Springer, Cham., 9 pp.

Zhang, Ruoqiao, et al., "A cascaded deep-learning reconstruction method for sparse-view kV-switching dual-energy CT", A sinogram inpainting method based on generative adversarial network for limited-angle computed tomography. In 15th International Meeting on Fully Three-Dimensional Image Reconstruction in Radiology & Nuclear Medicine., 8 pp.

Zhou, Bo, et al., "Generation of Virtua Dual Energy Images from Standard Single-Shot Radiographs using Multi-scale and Conditional Adversarial Network", In Asian Conference on Computer Vision (pp. 298-313). Springer, Cham., 17 p.

* cited by examiner

PROCESSING DEVICE FOR OBTAINING GAP FILLER SINOGRAM INFORMATION, COMPUTER TOMOGRAPH, METHOD AND COMPUTER PROGRAM

CROSS-REFERENCE TO RELATED APPLICATION

This application claims priority from European Patent Application No. EP 21162349.1, which was filed on Mar. 12, 2021, and is incorporated herein in its entirety by reference.

Embodiments according to the invention relate to a processing device for obtaining gap-filler sinogram information.

Some embodiments according to the invention relate to a computer tomograph (computed tomography scanner) comprising a processing device for obtaining gap-filler sinogram information.

Some embodiments according to the invention relate to a method of obtaining gap-filler sinogram information.

Other embodiments according to the invention relate to a computer program.

Embodiments of the invention relate to a processing device for completing incomplete dual-energy CT data while using deep neural networks to reduce exposure time and/or to reduce dose, and relate to a method and to a computer program.

BACKGROUND OF THE INVENTION

X-ray computer tomography (CT) is an imaging method widely used in medicine and also in industrial applications. In this process, a relatively large number (typically hundreds to thousands) of transmission images (radiographic images) are captured in different projection directions. The representation of a spatial dimension (a row of detector pixels perpendicular to the axis of rotation) and of the angular dimension (angle of rotation between the object and the imaging system) is referred to as a sinogram. Subsequently, a tomographic cross-sectional image can be reconstructed from this sinogram [1]. Assuming a detector with multiple detection lines, it is equally possible to reconstruct multiple layers from the pixel rows perpendicular with respect to the axis of rotation (i.e., multiple sinograms, for example) simultaneously [2]. Thus, the data structure containing the projection data of such a multi-line detector (i.e., the sinogram in a broader sense) is three dimensional. In the following, we will use the notation in which the first dimension ("x") describes the pixel number along the line, the second dimension ("y") describes the line number, and the third dimension ("z" or "α") describes the angular increment. Usually, this first dimension of such an extended sinogram is essentially perpendicular to the axis of rotation, while the second dimension is essentially parallel to the axis of rotation.

Now, on the one hand, capturing of such X-ray projections involves a certain amount of time and is associated with a certain (potentially harmful) dose exposure [3] for the patient or the examination object. Both are to be kept as small as possible for obvious reasons. In medical applications, the focus is on reducing the dose, whereas in technical-industrial applications with inanimate examination objects, the focus is on the duration of exposure (and, thus, on the achievable work cycle). On the other hand, a high-quality CT image involves a sufficiently large number of these projection images captured. Too short an exposure time and/or too small a number will usually result in blurrier and/or noisier CT images.

The dual-energy method (or two-energy method) is a technique well-known in computer tomography ("dual-energy CT," two-energy computer tomography, multi-energy X-ray, or two-spectrum CT) to reduce beam hardening artifacts [4, 5, 6]. Furthermore, dual-energy CT allows not only to correct beam hardening artifacts in CT, but also to obtain additional material information about the examined object [7, 8].

Dual-energy CT involves two CT data sets with different spectral parameters, these are simply referred to as "low energy" (LE, low energy) and "high energy" (HE, high energy). Adjusting the spectral parameters may include, e.g., a change in the accelerating voltage of the X-ray tube and/or the use of additional pre-filters.

To capture dual-energy data, one may either capture two scans in succession at different spectral parameters or capture two scans simultaneously while using two X-ray sources and two detectors. In both cases, this results in approximately doubling of the dose, in addition to doubling of the exposure time in the first case, and in addition to doubling of the cost of the X-ray hardware and results in overall increased design complexity in the second case.

One of several possible implementations of dual-energy CT typically consists of the following steps: firstly, the projection data for a standard CT is captured. Then, a second CT projection data set having adjusted spectral parameters is captured (e.g., change in accelerating voltage and/or pre-filter). The exposure time and the dose are thus increased. Additional hardware is not necessary. These two data sets are further processed while using dual-energy methods (two-energy methods), followed by CT reconstruction of the cross-sectional images. Alternatively, the second data set having the other spectral parameters may be captured simultaneously with a second set of X-ray components (consisting of at least an X-ray source and a detector). This has no influence on the subsequent steps of data processing.

In the following, some disadvantages of dual-energy methods will be described:

On the one hand, capturing of such X-ray projections involves a certain amount of time and is associated with a certain (potentially harmful) dose exposure for the patient or the examination object. Both are to be kept as small as possible for (obvious) reasons. In medical applications, the focus is on reducing the dose, whereas in technical-industrial applications with inanimate examination objects, the focus is on the capturing duration (and, thus, on the achievable work cycle). On the other hand, a high-quality CT image involves a sufficiently large number of these projection images. Too small a number usually results in blurrier and/or noisier CT images.

Thus, according to conventional technology, dual-energy CT, even in various implementations, comes with a disadvantage: increased dose and increased exposure time or increased dose and increased equipment expenditure. As a result, dual-energy CT can only be used economically in relatively few, specific applications, although the information gain may be significant in many more cases [9].

Dual-energy CT is a good way to increase contrast between materials in the 3D volume or to correct artifacts in the 3D volume. However, dual-energy CT measurement involves (at least in some cases) at least two complete CT measurements of the same object at different spectral parameters. This is done either by performing a second measurement or a cross setup, which consists of 2 CT systems. What is problematic here is the increase in the measuring time (factor 2) or the increase in the system costs (second CT system). On the one hand, deep-learning approaches are increasingly used to achieve improvements in image processing also of dual-energy X-ray data [10]. On the other hand, methods for artificial generation of X-ray projection images while using generative neural networks have been known [11].

From the point of view of CT reconstruction, missing images of certain projection angles represent gaps in the sinogram. Methods for CT reconstruction of sinograms having gaps have been known that are based on deep-learning methods and use, e.g., GANs for reconstruction [12] or methods that extend incomplete sinograms while using GANs [13, 14, 15].

Furthermore, a dual-energy method has been known that, in the case of a limited field of view in one of the two imaging chains ("limited field of view") in the reconstructed voxel volume (i.e., not at the level of the projections or sinograms), estimates the missing regions while using the structural information from the other, complete imaging chain so as to obtain a complete data set [16]. This method assumes a dual source system wherein the HE imaging component has a reduced FoV (Field of View). These truncated HE projections are alternatively completed with the rescaled data from the LE system to avoid reconstruction artifacts. This works sufficiently well for a known examination object like the human body in terms of avoiding said image errors in the reconstruction. However, as a consequence, this does not allow dual-energy evaluation in this area. The deep-learning system, however, works on the voxel data sets and generates the missing regions of the limited FoV while using deep-learning methods.

Therefore, there is a desire to remedy or at least partially remedy the aforementioned drawbacks in dual-energy CT. In addition, there is a desire to provide a processing device that ensures (for example, in a simple and inexpensive manner) a lower radiation dose and/or shorter measuring time and, thus, lower cost.

Overall, there is a desire to provide a concept that involves an improved trade-off between image quality, radiation dose, measuring time, and cost.

SUMMARY

An embodiment may have a processing device for obtaining gap-filler sinogram information, the processing device being adapted to obtain first sinogram information associated with a first spectral parameter, and to obtain second sinogram information associated with a second spectral parameter, and the processing device being adapted to obtain the gap-filler sinogram information which is associated with the second spectral parameter and which fills the one gap in the second sinogram information, on the basis of the first sinogram information and the second sinogram information.

Another embodiment may have a computer tomograph including at least one inventive processing device.

According to another embodiment, a method for obtaining gap-filler sinogram information may have the steps of: obtaining first sinogram information, wherein the first sinogram information includes information associated with a first spectral parameter, obtaining second sinogram information, wherein the second sinogram information includes information associated with a second spectral parameter, determining gap-filler sinogram information that fills a gap in the second sinogram information, on the basis of the first sinogram information and the second sinogram information.

Yet another embodiment may have a computer program including instructions that, when the program is executed by a computer, cause the computer to perform the inventive methods.

According to still another embodiment, a non-transitory digital storage medium may have a computer program stored thereon to perform the inventive methods, when said computer program is run by a computer.

Further features and details of the invention are apparent from the subclaims, the description and the drawings. Within this context, features and details which are described in connection with the processing device according to the invention are of course also valid in connection with the computer tomograph according to the invention and vice versa in each case, so that with respect to the disclosure, mutual reference is or can typically be made to the individual aspects of the invention.

In other words, the methods disclosed herein may optionally be supplemented by any features, functionalities and details disclosed herein with respect to the devices, both individually and in combination.

The devices disclosed herein may optionally be supplemented by any features, functionalities and details disclosed herein with respect to the methods, both individually and in combination.

One embodiment according to the invention provides a processing device for obtaining gap-filler sinogram information. The processing device is adapted to obtain first sinogram information associated with a first spectral parameter. The processing device is further adapted to obtain second sinogram information associated with a second spectral parameter different from the first spectral parameter. The processing device is further adapted to obtain gap-filler sinogram information which is associated with the second spectral parameter and which fills a gap in the second sinogram information, on the basis of the first sinogram information and the second sinogram information. Obtaining sinogram information herein may also be synonymous with receiving or determining sinogram information.

This embodiment is based on the understanding that a gap of second sinogram information can be filled with the information already contained in the obtained (e.g., received) first sinogram information while using the first and second sinogram information to obtain gap-filler sinogram information. The advantages of dual-energy CT can thus be (at least substantially) preserved, such as correction of beam hardening artifacts or obtaining additional material information, such as the ability to distinguish different materials, even if the second sinogram information exhibits gaps (for example, was not captured for all angular values). Accordingly, an object to be examined may be exposed to less X-ray radiation because second sinogram information may contain gaps (i.e., e.g., may have been captured with fewer angular values) that may be (at least approximately) reconstructed via the first sinogram information and the second sinogram information by a processing device according to the invention, for example. Alternatively or complementarily, a processing device according to the invention may be operated more cost-effectively because, e.g., less time may be needed to generate or obtain second sinogram information exhibiting gaps as opposed to complete second sinogram information. By generating the gap-filler sinogram information, the advantages of dual-energy CT are (at least substantially) preserved. Rather than capturing the second data set in its entirety, the second CT measurement can advantageously be performed with significantly fewer angular increments. The angular increments missing in comparison with (or, as compared to) the first measurement are calculated/determined or estimated by a processing device according to the invention. Thus, it may be possible to generate dual-energy CT data sets with much shorter additional measuring time, which data sets may be used for artifact reduction or contrast enhancement. Advantages of the method are reduced costs (measuring time), and/or reduced doses and/or reduced equipment costs (no cross setup required). The features or the solution allows to take advantage of DE-CT without having to accept the—typically double—measuring time. The advantage is in cost saving and/or dose minimization.

Sinogram information refers, e.g., to the information that may be obtained with a projection in CT while using a detector. Sinogram information may include, e.g., further data such as timestamp, detector information, angular increment information, or similar information related to projection or detection. Sinogram information may refer, e.g., to sinogram pixels, lines (e.g., sinogram lines or sinogram rows of pixels) or sinogram patches (e.g., projection patches (patches of spatially adjacent pixels) or sinogram pixel groups), and/or the information content associated with the sinogram pixels, lines, or patches, such as one or more gray values. A sinogram is typically understood to be a 2D representation of the pixel values of a detector row along the projection angles. In the case of an area detector, one now does not have a single line, but many lines. The "extended" sinogram now no longer has two dimensions, but three; that is, two spatial dimensions (x and y directions within the detection plane, plus the angular increment as the third dimension). Sinogram information as used herein may refer to a sinogram in two dimensions as well as in three dimensions.

Gap-filler sinogram information as used herein may refer, e.g., to a synthesized sinogram pixel and/or to the information content associated with the synthesized sinogram pixel. Gap-filler sinogram information may include, e.g., further information such as a timestamp or coordinates associated with the pixel. Gap-filler sinogram information may, e.g., relate to a synthesized sinogram line and/or to the information content associated with the synthesized sinogram line. Gap-filler sinogram information may refer, e.g., to a synthesized sinogram patch and/or to the information content associated with the synthesized sinogram patch. According to embodiments, the processing device is adapted to generate gap-filler sinogram information while using first sinogram information and second sinogram information.

According to an advantageous embodiment of the invention, the gap corresponds to one or more pixels. For example, the gap may correspond to one or more pixel values. For example, a pixel may correspond to a gray value in the projection image in question. For example, a pixel value may correspond to information obtained from the pixel of the detector. A gap comprising multiple pixels or pixel values may correspond to, e.g., a row of pixels or a column of pixels. A gap comprising multiple pixel values may correspond to, e.g., an information gap in the sinogram information that corresponds to missing information from a row or a column. A gap that spans multiple pixels may correspond to a "patch" or an area of pixels. For example, a patch is an area of pixel values that includes, e.g., an extension in two coordinate directions of the sinogram. As mentioned above, it may mean a two dimensional sinogram or an extended 3D sinogram. For example, a patch may have a symmetric extension about the location coordinate of the gap, or an asymmetric extension about the location coordinate of the gap. For example, an extension may be larger in one coordinate direction of the sinogram (for example, a position along a linear image sensor) than in the other direction of the sinogram (for example, an angular direction). For example, an extension may be the same in both coordinate directions of the sinogram. An extension refers, e.g., to the number of pixels, or pixel values, in a coordinate direction. Coordinates refer, e.g., to an angular increment of the angular projections of a dual-energy CT. Therefore, the processing device may process the second sinogram information having gaps and may synthesize the information of the gap while using the first sinogram information and the second sinogram information. For example, a gap may comprise more than one pixel (pixel value/grey value). For example, a gap may comprise 99% or less of the second sinogram information as compared to the first sinogram information. For example, a gap may comprise 95% or less of the second sinogram information as compared to the first sinogram information. For example, a gap may comprise 90%, 85%, 75%, 70%, 60%, 50%, 40%, 30%, 20%, 10% or less of the second sinogram information as compared to the first sinogram information. For example, a gap may comprise 1% or more of the second sinogram information as compared to the first sinogram information. For example, a gap may comprise 50% or more of the second sinogram information as compared to the first sinogram information. This means that, e.g., 90% of the angular projections present in the first sinogram information are not included in the second sinogram information. A gap then corresponds to, e.g., 90% of the second sinogram information as compared to, e.g., angular projections of the first sinogram information. A gap may (also) refer to the absence of data or pixels in the second sinogram information as compared to the first sinogram information. According to the desired or more than recommended quality of the dual-energy method, a gap of the second sinogram information (for example, a size of the gap(s) of the second sinogram information as compared to the first sinogram information) may be set or pre-determined. Gap does not refer to contiguous information. For example, a gap refers to the missing information, considered together, of a second sinogram information as compared to a first sinogram information.

Advantageously, it is possible, e.g., to perform a dual-energy method with a reduced resolution (for example, angular resolution) of the second sinogram information that corresponds to a gap of the second sinogram information as compared to the first sinogram information (or which results in gaps in the second sinogram information as compared to the first sinogram information), which dual-energy method is at least substantially equivalent to a result obtained with a dual-energy method without reduced resolution.

According to an advantageous embodiment, the processing device may be adapted to obtain the gap-filler sinogram information to obtain a resolution-enhanced version of the second sinogram information. For example, a resolution-enhanced version may have a higher angular resolution (than is present in the second sinogram information obtained as input variable). For example, a resolution-enhanced version of the second sinogram information may be obtained in that the processing device is adapted to fill an (angular) gap of the second sinogram information with gap-filler sinogram information, for example in that the gap-filler sinogram information is added to the second sinogram information. Therefore, it is possible to obtain resolution-enhanced second sinogram information while using a processing device of the invention according to embodiments, on the basis of first sinogram information and (resolution-reduced) second sinogram information. A resolution of second sinogram information that is intentionally reduced by the user of a dual-energy CT may advantageously result in a reduced exposure time and/or in a reduced radiation dose.

According to an advantageous embodiment, the first sinogram information may have a first angular resolution. The second sinogram information may have a second angular resolution that is smaller than the first angular resolution. The processing device may be adapted to obtain the gap-filler sinogram information for an angular value that is between two angular values of the second sinogram information.

In order to distinguish sinogram information (input sinogram information) obtained from the processing device from sinogram information obtained while using gap-filler sinogram information, sinogram information that includes gap-filler sinogram information may be referred to as output sinogram information. Advantageously, therefore, when the resolution of the second sinogram information is reduced by, e.g., 50%, an exposure time for the second sinogram information may be reduced by 50% in sequential picture-taking.

According to an advantageous embodiment, the second sinogram information for obtaining the gap-filler sinogram information may be (second) sinogram information comprising sinogram information neighbors, of the gap, of the second sinogram information.

Depending on the gap, sinogram information neighbors comprise a corresponding set of pixels. For example, sinogram information neighbors of a gap comprising a pixel may comprise those pixels that are in close proximity to the gap. Here, a neighborhood may be defined with, e.g., a pixel-wise, absolute, or relative distance from the gap. Sinogram information neighbors may therefore be, e.g., pixels directly adjacent to a pixel of a gap and/or may be pixels spaced from the gap with at least one or more pixels therebetween. A sinogram information neighborhood may include, e.g., pixels having a maximum pixel-wise distance, or a distance that is defined in pixel pitches, from the gap, where a maximum pixel-wise distance may be a distance having an integer number of pixels in, e.g., one or more directions in the pixel coordinate system. A sinogram information neighborhood may comprise a different or the same pixel-wise distance in a first coordinate direction than/as in another, second coordinate direction. Correspondingly, the same is applicable to gaps corresponding to a pixels row or a pixel patch. Advantageously, gap-filler sinogram information can be reconstructed, or synthesized, in accordance with the sinogram information neighbors. Sinogram information neighbors may be defined differently, for example by a user, depending on the gap and/or the object to be examined, so as to enhance a quality of gap-filler sinogram information. Sinogram information neighbors may be chosen differently for each gap.

Advantageously, e.g., structural information encoded in first sinogram information can be used for reconstruction or synthesis of gap-filler sinogram information that fills a gap in the second sinogram information. For example, a distance from a gap in one direction may comprise no pixel (no pixel only for the distance from a gap in first sinogram information), one pixel, or more than one pixel. For example, a distance from a gap in one direction may comprise less than 100 pixels, less than 50 pixels, less than 20 pixels, or less than 10 pixels. Sinogram information neighbors may comprise fewer or more pixels for first sinogram information than for second sinogram information. Advantageously, the influence of first sinogram information and/or second sinogram information in obtaining gap-filler sinogram information can be adjusted by the processing device with the pixels of the first sinogram information and the second sinogram information that are comprised by sinogram information neighbors. Another advantage may be that a displacement of pixels of the first sinogram information to pixels of the second sinogram information, which may occur, e.g., when the respective sinogram information is captured sequentially, may be at least partially compensated for by a suitable selection or pre-determination of sinogram information neighbors.

According to an advantageous embodiment, the processing device may be adapted to obtain the gap-filler sinogram information on the basis of one or more sinogram values (sinogram information neighbors) of the second sinogram information that are adjacent to the gap, and additionally on the basis of one or more sinogram values (sinogram information neighbors) of the first sinogram information that are adjacent to the gap, and/or one or more sinogram values of the first sinogram information that are associated with the gap.

Neighboring may refer, e.g., to an angular neighborhood or a spatial neighborhood. An angular increment in CT imaging has been known to be smaller, or significantly smaller, than 1°, for example. A gap occurs, e.g., when second sinogram information is captured with reduced sampling (e.g., a reduced angular resolution) as compared to first sinogram information. What is meant by reduced sampling is, e.g., sampling with larger angular increments.

According to an advantageous embodiment, the first sinogram information for obtaining the gap-filler sinogram information may be first sinogram information comprising sinogram information neighbors, of the gap, of the first sinogram information, and first sinogram information of the gap.

For example, information concerning the sinogram information neighbors may be included in the respective sinogram information. Advantageously, depending on the sampling of the second sinogram information, a processing device may obtain information concerning sinogram information neighbors of the second sinogram information. The information on the sinogram information neighbors of the second sinogram information may be included in the second sinogram information obtained from the processing device. For example, the second sinogram information may be examined for gaps on a pixel-by-pixel basis or in patches comprising multiple pixels, and/or the gaps known from the scan may be used. For example, for a corresponding gap, sinogram information neighbors can then be determined which are advantageous for determining the gap-filler sinogram information. The processing device may be adapted accordingly for this purpose.

According to an advantageous embodiment, the processing device may be adapted to obtain the first sinogram information and the second sinogram information simultaneously with one scan or sequentially with two scans.

As already described above, various systems have been known. A dual-energy CT may have corresponding hardware capable of detecting first sinogram information and second sinogram information simultaneously, or may have hardware capable of performing only one scan with one spectral parameter. First sinogram information and second sinogram information may therefore be obtained simultaneously or with a time delay. Advantageously, the processing device may be adapted to obtain (determine) gap-filler sinogram information in each of the cases. For simultaneously obtained sinogram information, the processing device may advantageously reduce a radiation dose by determining second sinogram information exhibiting gaps, wherein the gap-filler sinogram information is obtained (determined) from the processing device (for example, computationally).

A further scan to correct and/or complete the second sinogram information exhibiting gaps is not necessary, or is omitted. For sequentially obtained sinogram information, the processing device can advantageously reduce a radiation dose and/or an exposure time by determining the second sinogram information exhibiting gaps (for example, by determining the second sinogram information with a reduced number of angular increments). A further scan for correction and/or completion of the second sinogram information exhibiting gaps is not necessary, or is omitted. Advantageously, the obtained (determined or synthesized) sinogram information may replace and/or supplement sinogram information obtained from a scan.

According to an advantageous embodiment, the first sinogram information may comprise a plurality of transmission image lines or transmission images, the transmission images being associated with different (transmission) angles and being associated, e.g., with a first fluoroscopic peak wavelength or a first fluoroscopic accelerating voltage. The second sinogram information may comprise a plurality of transmission image lines or transmission images associated with different transmission angles and associated with, e.g., a second fluoroscopic peak wavelength or a second fluoroscopic accelerating voltage, wherein the first sinogram information and the second sinogram information are associated with different transmission beam energies of a dual-energy CT (multi-energy computer tomography).

Different transmission beam energies may be achieved, e.g., by using different accelerating voltages and/or by using different pre-filters or additional pre-filters. Dual-energy CT may be a designation for a multi-energy computer tomograph or for multi-energy computer tomography. Multi-energy refers to the computer tomograph being adapted to perform computer tomography while using more than one spectral parameter.

The processing device may use a mathematical method, such as a polynomial fit or a neural network, to obtain the gap-filler sinogram information. The processing device may be adapted to use one or more mathematical methods and/or a neural network to obtain gap-filler sinogram information.

For example, in a mathematical method such as a polynomial fit, five projections may be used as input data. In the following, an example with HE projections (e.g., projections with high energy or high accelerating voltage) as second sinogram information and LE projections (e.g., projections with comparatively lower energy or comparatively lower accelerating voltage) as first sinogram information is executed. This is for illustrative purposes only, and it is understood that HE projections may also be present as first sinogram information and that LE projections may also be present as second sinogram information.

According to an advantageous embodiment, the processing device may be adapted to obtain the gap-filler sinogram information while using a neural network.

For example, a Deep Neural Network (DNN), e.g. a Generative Adversarial Network (GAN), a Convolutional Neural Network (CNN), a U-Net architecture, or a combination of one or more of the foregoing may be used to obtain gap-filler sinogram information. For example, these may be adapted to obtain gap-filler sinogram information pixel by pixel, patch by patch, or frame by frame. The gap-filler sinogram information may be obtained, e.g., by providing the first and second sinogram information (or a portion thereof) as input information to the neural network. For example, the neural network may generate structural information of the second sinogram information from the structural information of the first sinogram information so that gap-filler sinogram information is obtained. The neural network may be adapted to supplement the second sinogram information with gap-filler sinogram information such that a resolution of the second sinogram information corresponds at least substantially to a resolution of the first sinogram information. Advantageously, from the obtained second sinogram information (output sinogram information) and the first sinogram information, e.g., material information about the examined object may be obtained and/or, e.g., beam hardening artifacts may be reduced. Advantageously, the processing device may be adapted to obtain material information about the examined object from output sinogram information and first sinogram information, and/or to reduce beam hardening artifacts.

Advantageously, by using a neural network, the second sinogram information may be obtained (generated or synthesized), which at least substantially corresponds to second sinogram information generated without gaps. By deliberately determining the second sinogram information with gaps (e.g., with reduced angular resolution), a scan time may advantageously be reduced and/or a radiation dose may be reduced, and the gaps may then be computationally filled, e.g., while using the neural network. Incidentally, it has been recognized that a neural network is particularly well suited to exploit dependencies between the first sinogram information and the second sinogram information in filling the gaps. For example, the neural network may be trained with gap-free sinogram information (and may be adapted, e.g., to the characteristics of the object to be analyzed or of a corresponding object class, e.g., human being or technical object, or may be adapted to the specific conditions of a CT array). Thus, after completion of the training, the neural network can fill in the gaps in the second sinogram information in a particularly reliable manner and with high accuracy, whereby a loss of resolution or of sharpness due to the gaps in the original second sinogram information may be kept low.

According to embodiments, the neural network may comprise at least one of CNN, GAN, and U-Net.

For example, at least one of said neural networks or architectures may be used, or even at least two of said neural networks or architectures may be connected in series or in parallel. Different or similar neural networks may be interconnected and/or be successive. Embodiments of the invention are not limited to said neural network architectures. Other architectures may be employed for a neural network. In particular, it has been shown that the aforementioned types of neural networks are particularly well suited for the present application.

In this way, the projections of second sinogram information may be generated pixel by pixel, patch by patch, or image by image, or the gaps in the sinogram of the second sinogram information may be closed; the structural information about the object is already known from the scan of the first sinogram information, and only the energy-specific differences need to be generated.

According to embodiments, first the first sinogram information may initially be measured for any angular increments. In the next step, the second sinogram information may be captured while omitting, e.g., every second angular increment (i.e., with half the angular resolution). In other words, the second sinogram information may be measured for, e.g., every second angular increment, third angular increment, fourth angular increment, fifth angular increment, or $n^{th}$ angular increment. Combinations of different angular increments are also possible. For example, to allow training of the neural network, some projections may be captured for the missing angular increments. Then there will be enough data to provide a training data set.

To train the neural network, the training data may be augmented, e.g., and/or further techniques to prevent overfitting may be applied, such as regularization, dropout (omission of values), noise, early stopping.

The parameters optimized during the training of the neural network may be initialized, e.g., either randomly or by parameters from a pre-trained network with the same architecture that has been successfully trained to solve a similar problem (transfer learning).

Further details regarding some of the machine-learning/deep-learning techniques mentioned here can be found in specialized literature and may also be applied here.

The architecture of the CNN described here by way of example is a primitive realization of the approach to find a solution. In practical implementation, a neural network based on the U-Net architecture has been shown to be accurate. However, it is also possible to use other network architectures of a neural network that in some cases may outperform the efficiency of the U-Net described here. These may be adapted, e.g., to obtain gap-filler sinogram information according to the invention.

Advantageously, the neural network is trained and/or organized such that it can obtain gap-filler sinogram information while using first and second sinogram information.

Another embodiment provides a computer tomograph (computed tomography scanner) comprising at least one processing device, for example according to the embodiments disclosed herein.

Advantageously, the computer tomograph may complete second sinogram information exhibiting gaps while using the processing device (while using the first sinogram information and the second sinogram information). Advantageously, the computer tomograph may at least substantially reduce a radiation dose for, e.g., a patient or an object, and/or may at least substantially reduce an exposure time of dual-energy CTs, depending on a configuration of the computer tomograph having one emitter and one detector or having multiple emitters and, correspondingly, multiple detectors.

Another embodiment provides a method of obtaining gap-filler sinogram information. The method comprises obtaining first sinogram information, wherein the first sinogram information is associated with a first spectral parameter, obtaining second sinogram information, wherein the second sinogram information is associated with a second spectral parameter (wherein the second spectral parameter is different from the first spectral parameter). The method further comprises determining gap-filler sinogram information that fills a gap in the second sinogram information, on the basis of the first sinogram information and the second sinogram information.

This embodiment is based on the understanding that structural information of the detected object may be included in the first sinogram information, and that a gap in second sinogram information may be determined on the basis of the first sinogram information and structural information that may be included in those parts of the second sinogram information that do not have gaps. This may be achieved, e.g., by mathematical methods or by using a neural network.

According to an advantageous embodiment, the second sinogram information contains less information than does the first sinogram information. Less information may mean, e.g., that in an capturing method of obtaining first sinogram information and second sinogram information, an angular increment in capturing the second sinogram information is larger than an angular increment in capturing first sinogram information. In a dual-energy CT that may generate first sinogram information and second sinogram information simultaneously, less information may mean that the second sinogram information is generated with fewer detector pixels than is the first sinogram information. For example, (more) defective pixels may be present in the second sinogram information. Advantageously, defective pixels ("bad pixels") may be compensated for by obtaining gap-filler sinogram information.

According to an advantageous embodiment, determining the gap-filler sinogram information may comprise first sinogram information and second sinogram information. In this regard, the first sinogram information and the second sinogram information may each comprise (or use) spatial sinogram information neighbors, of the gap, of the second sinogram information, and the first sinogram information may (also/additionally) comprise first sinogram information of the gap (which corresponds to the gap of the second sinogram information). That is, the data set of the first sinogram information at the spatial location of the gap of the second sinogram information has information that is first sinogram information and is associated with the first spectral parameter. The information of the gap that is first sinogram information (which is present only in the first sinogram information) may be used to obtain gap-filler sinogram information (second sinogram information of the gap). Advantageously, e.g., an influence of the first sinogram information and of the second sinogram information may be controlled via the sinogram information neighbors of the respective sinogram information.

According to an advantageous embodiment, the first sinogram information may have a first angular resolution, and the second sinogram information may have a second angular resolution that is smaller than the first angular resolution. Determining the gap-filler sinogram information may further comprise filling the gap (in the second sinogram information) with gap-filler sinogram information. In this regard, e.g., gap-filler sinogram information obtained from the first and second sinogram information may be inserted into the second sinogram information at the (spatial) location of the gap (of the second sinogram information). For example, this may increase a resolution of the second sinogram information at the location of the gap. For example, despite gap(s) in the second sinogram information, this may at least substantially preserve the advantage of a dual-energy CT.

According to an advantageous embodiment, the spatial sinogram information neighbors may comprise sinogram information in surroundings $(2p+1)\times(2q+1)$. And sinogram information neighbors of the first sinogram information comprise sinogram information (with coordinates) ($[x+/-p, y+/-q, \alpha]$), and sinogram information neighbors of the second sinogram information comprise sinogram information (with coordinates) ($[x+/-p, y+/-q, \alpha-r]$) and ($[x+/-p, y+/-q, \alpha+r]$). Here, p may be a pixel-wise deviation in a first direction x that is substantially perpendicular to a projection angle $\alpha$, q may be a pixel-wise deviation in a second direction y that is substantially parallel to a axis of rotation of the projection angle $\alpha$ and to the first direction x, and r may be an angular deviation, for example in degrees or angular increments. Consequently, $x+/-p$ and $y+/-q$ here denote a rectangular image section, specifically in the x direction from the position $x-p$ to $x+p$, in the y direction from $y-q$ to $y+q$. Other coordinate conventions may also be used. Here, determining the gap-filler sinogram information may be based on sinogram information neighbors of the first and second sinogram information. For example, p, q, and r may be natural numbers in the case where r denotes an angular increment, otherwise r may be an angle in degrees. r may depend, e.g., on the angular resolving power of the dual-energy CT. For example, a single pixel may be denoted (identified) by ([x, y, α]), a line by, e.g., ([x, y+/−q, α]) or ([x+/−p, y, α]), patches correspondingly by ([x+/−p, y+/−q, α]). p and q may be the same or different. For example, symmetric sinogram information neighbors may be defined by an equal p and q, and asymmetric sinogram information neighbors may be defined by different values for p and q. Advantageously, by selecting the values, the input data may be adjusted. For example, it is possible to generate not only a single missing pixel at a time, but a contiguous area of pixels (for example lines or patches), for example rectangular image sections. This changes little in the formal notation as used above; for example, x and y will then not be coordinates of a single pixel, but contiguous intervals. For example, according to embodiments, the processing device may be adapted to select values for p, q and r, advantageously for one and/or more gaps. For example, (irregular) gaps may be surrounded by a constant or a variable number of sinogram information neighbors in the respective directions. For example, an L-shaped gap may thus be defined with, e.g., sinogram information neighbors comprising 2 pixels in each direction away from the gap. Other (irregular) gap shapes may occur. This may have the advantage that sinogram information neighbors are adapted to the gap and that a quality of the gap-filler sinogram information is increased during determining or obtaining.

According to an advantageous embodiment, the method may further comprise removing beam hardening artifacts, based on the first sinogram information, the second sinogram information, and the gap-filler sinogram information, and/or determining material information of the examined object, based on the first sinogram information, the second sinogram information, and the gap-filler sinogram information. For example, removing beam hardening artifacts may be performed by a beam hardening removal module. For example, the beam hardening removal module may be adapted to reduce a beam hardening effect on the basis of the first sinogram information, the second sinogram information, and the gap-filler sinogram information. For example, the beam hardening removal module may be an integral part of the processing device. Alternatively, the beam hardening removal module may be a separate module that is in data communication with the processing device. Material information may be determined by, e.g., a material information determination module. The material information determination module may be adapted, e.g., to determine one or more pieces of material information about the examination object on the basis of the first sinogram information, the second sinogram information, and the gap-filler sinogram information. For example, the material information determination module may be an integral part of the processing device. Alternatively, the material information determination module may be a separate module that is in data communication with the processing device. Advantageously, the quality of a beam hardening artifact removal and/or material information determination may be substantially the same when the second sinogram information exhibits gaps as when the second sinogram information exhibits no gaps. This may, e.g., reduce an exposure time and/or a radiation dose when determining material information and/or removing beam hardening artifacts.

According to an advantageous embodiment, prior to determining the gap-filler sinogram information, the method may comprise determining a registration of the first sinogram information with regard to the second sinogram information, and performing a registration of the first sinogram information with regard to the second sinogram information. This may be the case, e.g., when first sinogram information and second sinogram information are obtained sequentially. For example, an object, which may be a living being, may have moved or performed a breathing motion during the time between obtaining the first sinogram information and obtaining the second sinogram information, which may result in a relative displacement of the information obtained. Registration means may be used to at least substantially compensate for this offset in the information.

A further embodiment of the invention provides a computer program product. The computer program product comprises instructions which, when the program is executed by a computer, cause the computer to perform the method in accordance with embodiments of the invention.

According to embodiments of the invention, the object is achieved by a computer readable (storage) medium. The computer-readable (storage) medium comprises instructions which, when the instructions are executed by a computer, cause the computer to perform the method according to embodiments of the invention.

Thus, another embodiment of the method of the invention is a data stream or sequence of signals that constitute the computer program for performing any of the methods described herein. For example, the data stream or sequence of signals may be adapted to be transmitted over a data communication link, such as over the internet.

A further embodiment comprises a processing means, such as a computer or programmable logic device, configured or adapted to perform any of the methods described herein.

A further embodiment comprises a computer having installed thereon the computer program for performing any of the methods described herein.

A further embodiment according to the invention comprises a device or system adapted to transmit (e.g., electronically or optically) a computer program for performing any of the methods described herein to a receiver. The receiver may be, e.g., a computer, a mobile device, a storage device, or the like. The device or system may include, e.g., a file server for transmitting the computer program to the receiver.

In some embodiments, a programmable logic device (e.g., a field programmable gate array (FPGA)) may be used to perform some or all of the functionalities of the methods described herein.

In some embodiments, a field programmable gate array may cooperate with a microprocessor to perform any of the methods described herein.

In general, the methods are advantageously performed by any hardware device. The embodiments described above are merely illustrative of the principles of the present invention.

According to one aspect of the invention, the gap-filler sinogram information is not determined or calculated on the basis of data that has been further processed, such as voxels, but for example (directly) on the basis of the sinogram information.

BRIEF DESCRIPTION OF THE DRAWINGS

Embodiments of the present invention will be detailed subsequently referring to the appended drawings, in which.

Elements having the same function and mode of action each have been given the same reference numerals in FIGS. 1 to 7.

DETAILED DESCRIPTION OF THE INVENTION

Figure 1:
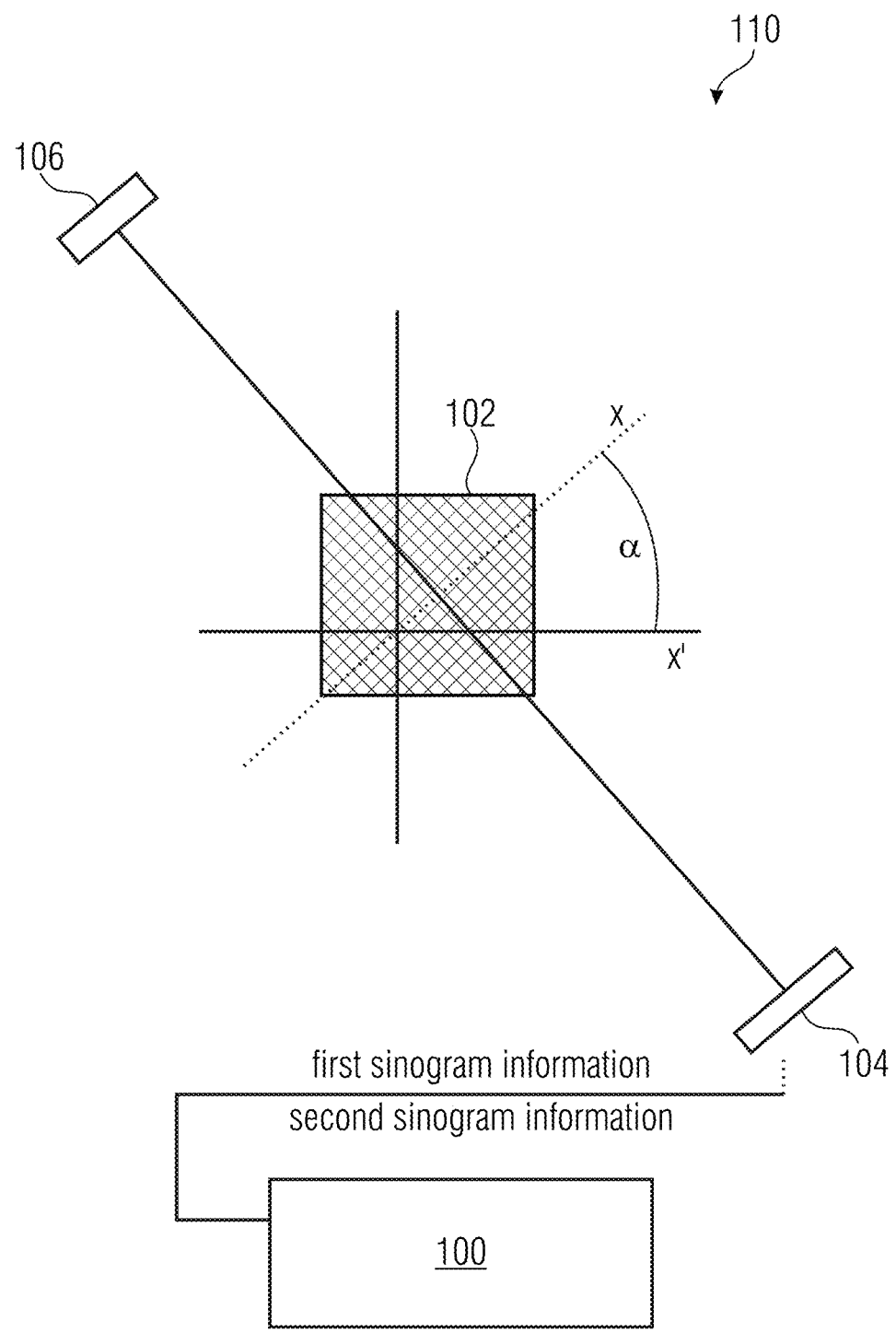
FIG. 1 shows a schematic representation of a computer tomograph with an object to be examined and a processing device for obtaining gap-filler sinogram information.

Typical embodiments of the invention will be described below with reference to the figures. In describing typical embodiments, the same reference numerals are possibly used for identical or similar parts in different figures and for different embodiments in order to make the description clearer. However, this does not mean that corresponding parts of the invention are limited to the variants illustrated in the embodiments.

1. Processing Device for Obtaining Gap-Filler Sinogram Information According to FIG. 1

In FIG. 1, an exemplary embodiment of a computer tomograph with a processing device according to the invention for obtaining gap-filler sinogram information is schematically shown. The computer tomograph according to FIG. 1 is designated by 110 in its entirety. The processing device according to FIG. 1 is designated by 100.

The processing device 100 for obtaining gap-filler sinogram information may be an integral part of the computer tomograph 110 or may be in data communication with the computer tomograph 110, as shown herein, to obtain first sinogram information and second sinogram information. Sinogram information is generated by means of X-ray computer tomography. Here, as mentioned above, methods have been known wherein one sinogram information is generated sequentially, and another sinogram information is generated basically simultaneously. FIG. 1 refers to a method of sequentially generating sinogram information. For this purpose, a radiator (source) 106 and a detector 104 are schematically shown which perform a projection through an object to be examined 102. The coordinate system used in the data capturing is typically coupled to the X-ray beam. The spatial coordinate y is perpendicular to the drawing plane (not shown). The coordinate x rotates along with α, i.e. is fixed with respect to the X-ray components 104 and 106, x' is fixed with respect to the examination object 102. A coordinate system with x, y and α references the sinogram information generated. The processing device 100 receives first sinogram information and second sinogram information. For example, a indicates an angle or angular increment with which the radiator 106 and the detector 104 are located with respect to the object. The processing device 100 obtains first sinogram information and second sinogram information from projections recorded by the detector 104. The detector may be a line detector or an area detector. After obtaining the first sinogram information and the second sinogram information, the processing device may generate gap-filler sinogram information. The gap-filler sinogram information may fill a gap in second sinogram information. For example, first sinogram information may correspond to information generated with "low-energy" (LE) spectral parameters. For example, second sinogram information may correspond to information generated with "high-energy" (HE) spectral parameters. For example, first sinogram information may alternatively be generated with HE spectral parameters, and second sinogram information may alternatively be generated with LE spectral parameters.

Accordingly, the detector 104 provides the first sinogram information and the second sinogram information to be processed by the processing device for obtaining gap-filler sinogram information.

2. Processing Device for Obtaining Gap-Filler Sinogram Information According to FIG. 2

Figure 2:
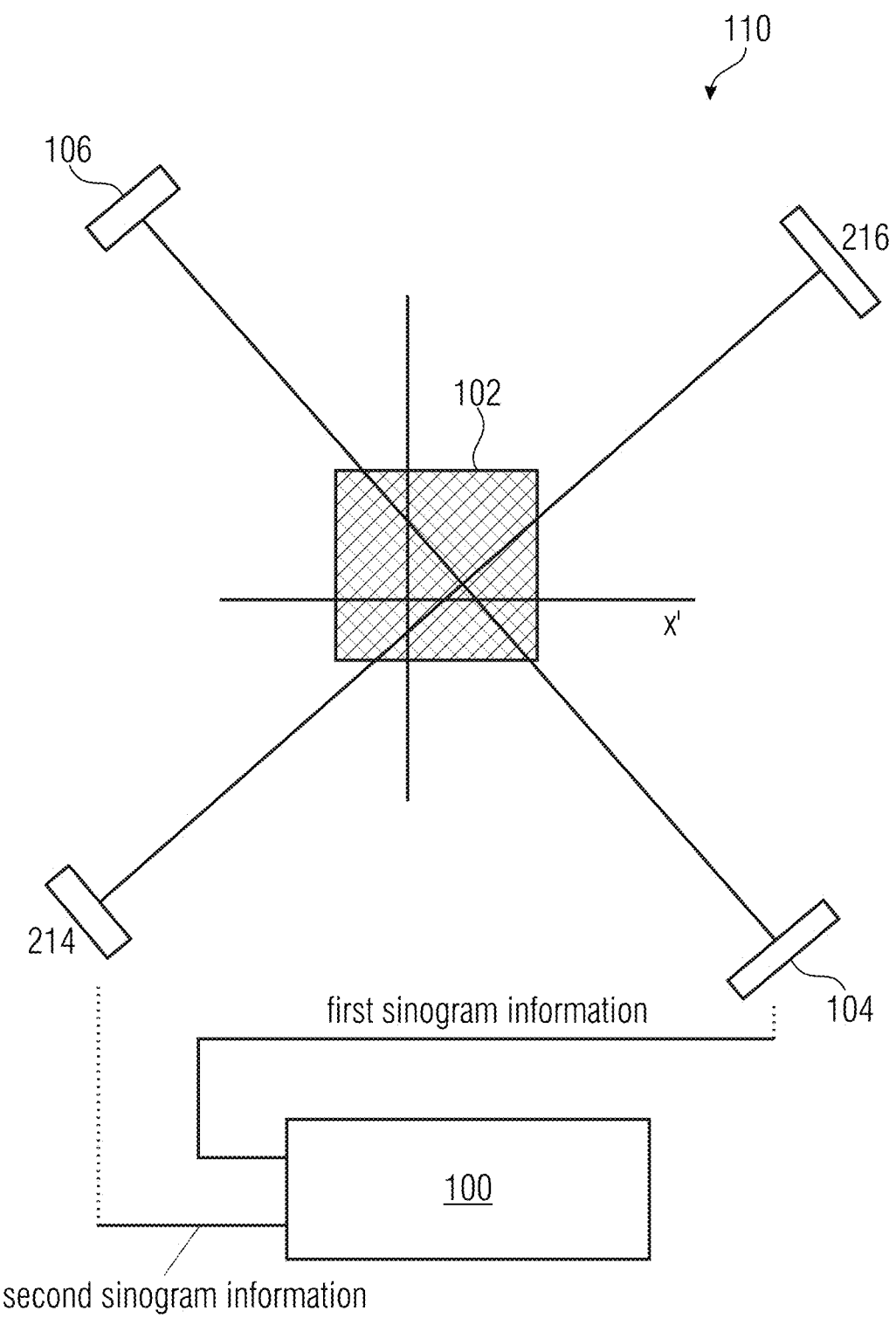
FIG. 2 shows a schematic representation of a computer tomograph with an object to be examined and a processing device for obtaining gap-filler sinogram information.

FIG. 2 differs from FIG. 1 in that a further emitter 216 and a further detector 214 are shown. This is a typical embodiment for capturing dual-energy CT essentially in parallel. The object 102 is simultaneously irradiated by radiation having different spectral parameters. Thus, first sinogram information is generated by a first detector (here detector 104), and second sinogram information is generated by a second detector (here detector 214), wherein the generated sinogram information of the first sinogram information and the second sinogram information each relate to the same transmission angle. Thus, a first projection associated with a first spectral parameter and a second projection associated with a second spectral parameter may be obtained for substantially the same projection direction. In the embodiment shown in FIG. 1, this is obtained by the same detector in two passes with different spectral parameters.

3. Processing Device for Obtaining Gap-Filler Sinogram Information According to FIG. 3

Figure 3:
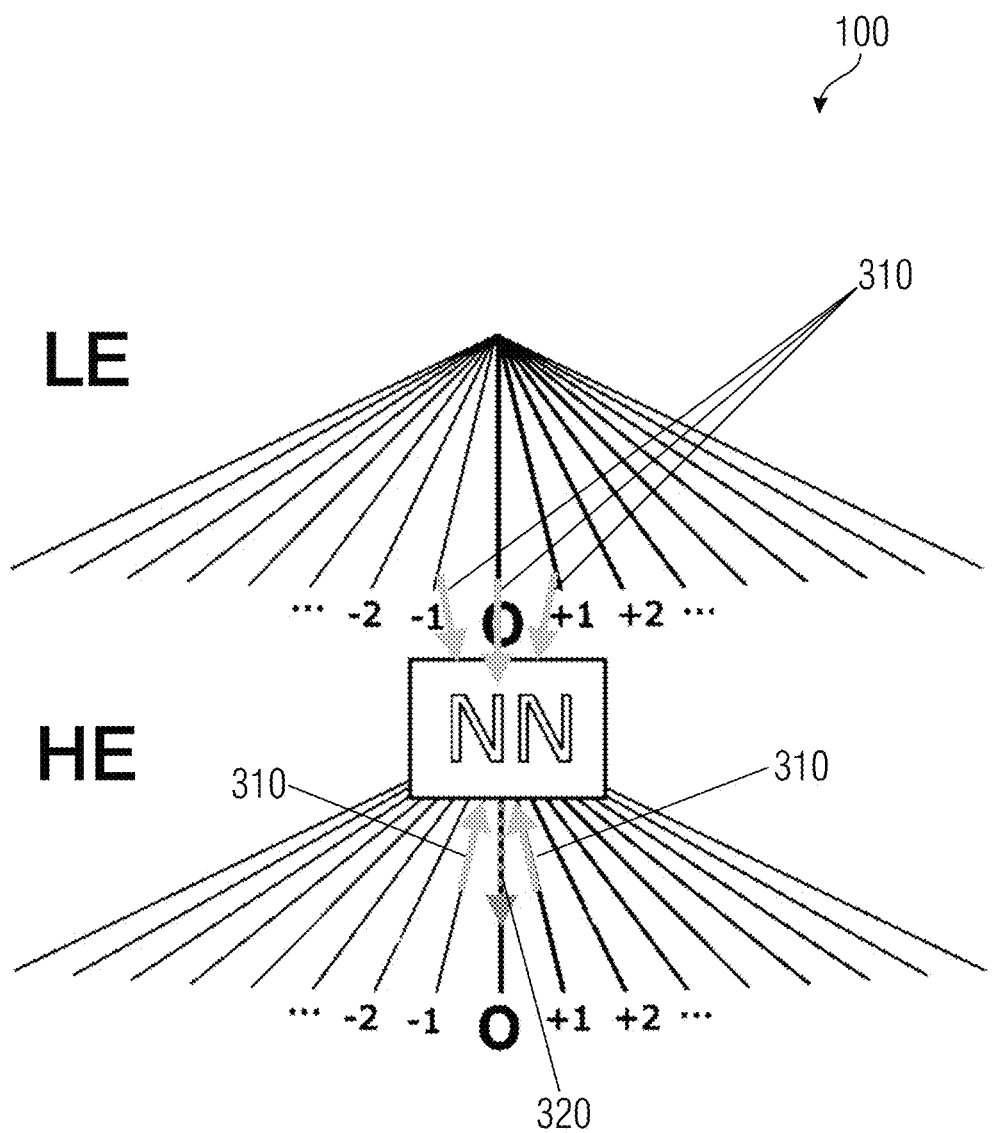
FIG. 3 shows a schematic representation of angular increments in projections of first sinogram information and second sinogram information in a processing device with generation of gap-filler sinogram information with a neural network.

FIG. 3 shows, by way of example, a processing device for obtaining gap-filler sinogram information 100 with exemplary different projections while indicating angular increments and a neural network (NN) adapted to obtain gap-filler sinogram information from first sinogram information and from second sinogram information. Here, the first sinogram information and the second sinogram information are denoted by LE and HE, respectively. For example, generation of gap-filler sinogram information may also be performed with HE as the first sinogram information and LE as the second sinogram information. The arrows (310)

shown in solid lines exemplify that first sinogram information (the arrows pointing into the neural network designated by NN from the top) and second sinogram information (the arrows pointing from the bottom) are processed by the neural network (NN) for obtaining gap-filler sinogram information, which is shown as a dashed arrow (320). The gap-filler sinogram information may be, e.g., the missing information of the second sinogram information, shown here at an angular increment 0, generated from the respective sinogram information of angular increments −1, +1 and 0 for first sinogram information (here LE), as already shown in examples above.

4. Method According to FIG. 4

Figure 4:
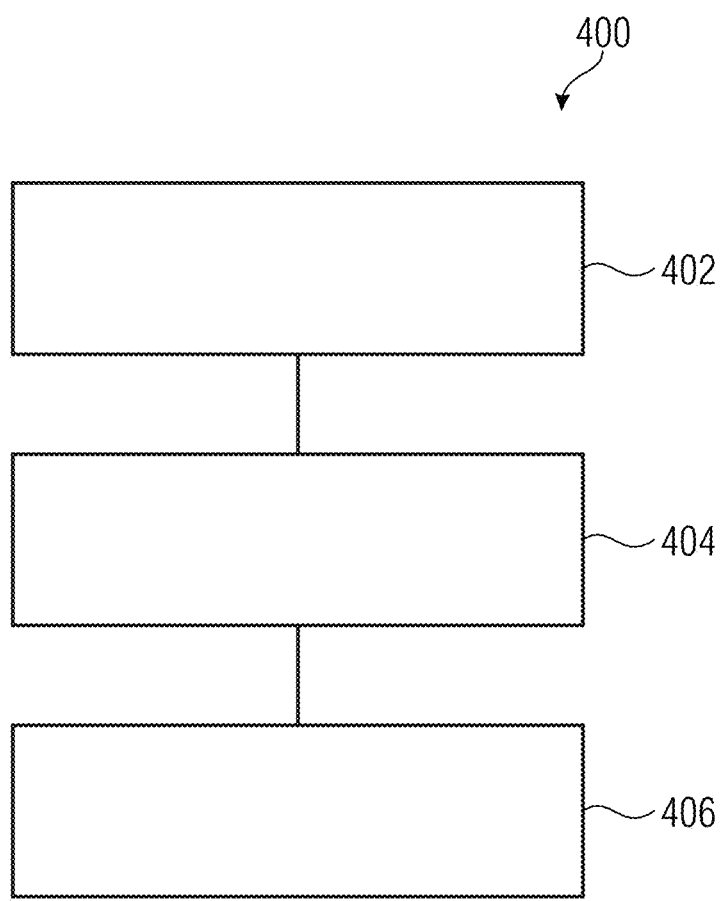
FIG. 4 shows a flowchart of a method of obtaining gap-filler sinogram information in a block diagram.

FIG. 4 shows, by way of example, a method 400 of obtaining gap-filler sinogram information in a block diagram. Here, 402 is obtaining first sinogram information, wherein the first sinogram information comprises information associated with a first spectral parameter. 404 relates to obtaining second sinogram information, wherein the second sinogram information comprises information associated with a second spectral parameter. And 406 relates to obtaining or determining gap-filler sinogram information that fills a gap in the second sinogram information, on the basis of the first sinogram information and the second sinogram information.

5. Method According to FIG. 5

Figure 5:
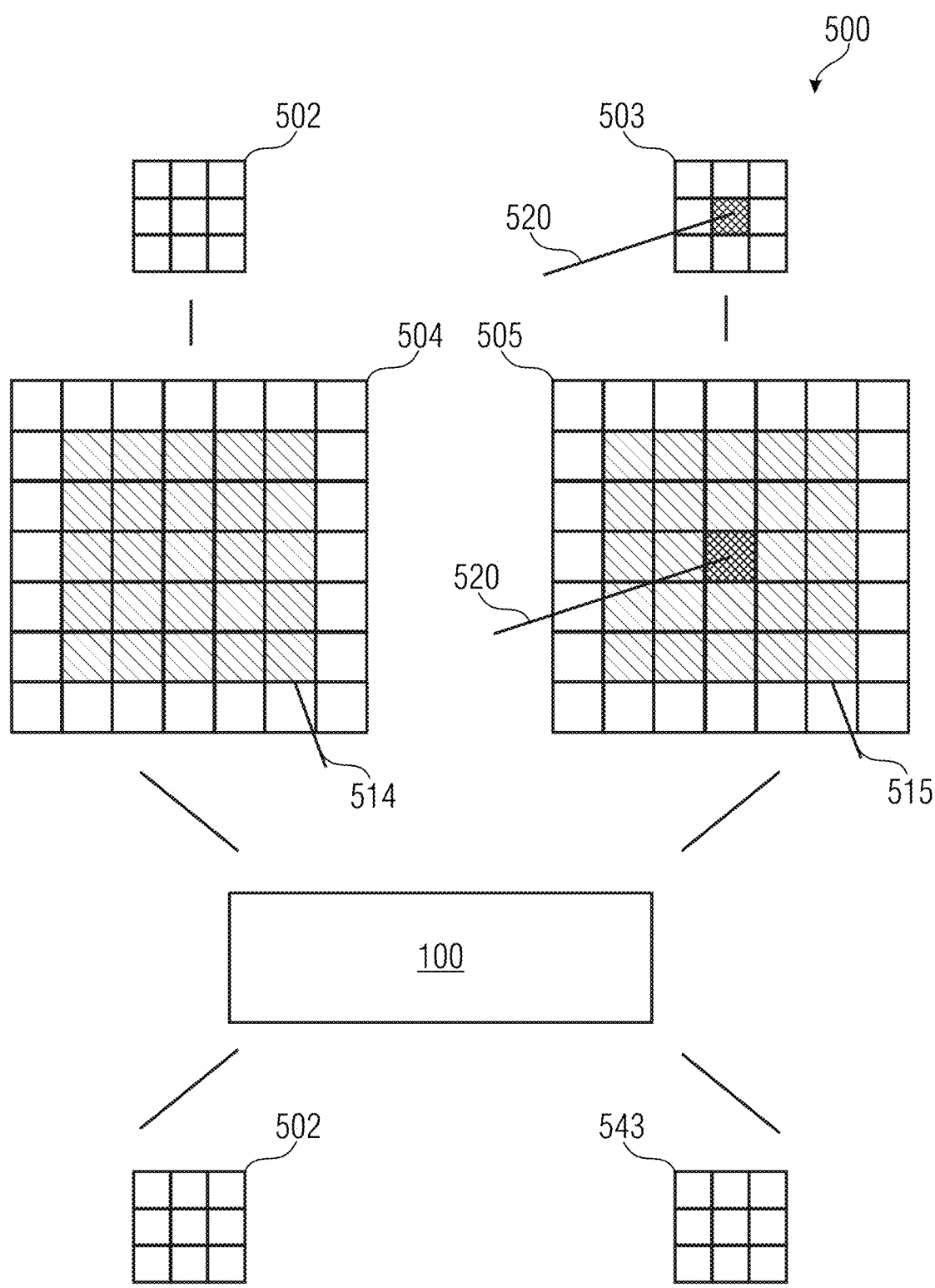
FIG. 5 shows a schematic representation of a method of obtaining gap-filler sinogram information for an exemplary gap comprising a pixel.

FIG. 5 shows, by way of example, a method 500 of obtaining gap-filler sinogram information for filling a gap 520, exemplarily comprising a pixel here, on the basis of first sinogram information 502 and second sinogram information 503. The extension of the pixel groups may be along spatial axes in the x and y directions. A spatial extension of the pixel groups may also be along the angle (for example, depending on the detector or setup). The processing device 100 is adapted to obtain gap-filler sinogram information while using the first sinogram information 502 and the second sinogram information 503, and to fill the gap 520 with the obtained gap-filler sinogram information. In other words, the processing device may fill a gap with synthetically generated gap-filler sinogram information. FIG. 5 shows a first obtained sinogram information 502 and second sinogram information 503, which relate to the same spatial pixels of the examined object. Here, the second sinogram information 503 has a gap 520 for which no sinogram information was obtained. 504 shows, by way of example, a first region of the first sinogram information spatially arranged around the first obtained sinogram information (including the first sinogram information 502). From the first sinogram region, a first sinogram reconstruction region 514 may be selected or pre-determined, e.g., by a pre-determined indication of the first sinogram reconstruction region, e.g., by a pre-determined extension in a first direction and a second direction (which is different from a first direction), wherein the extension (for example, pixel-wise) in the first direction may be larger or smaller than the extension in the second direction. The sinogram information included in the first sinogram reconstruction region may also be referred to as (first) sinogram information neighbors, wherein first sinogram information neighbors also include the sinogram information of the gap.

FIG. 5 further shows, e.g., a second region 505 of the second sinogram information spatially arranged around the second obtained sinogram information. From the second sinogram region, a sinogram reconstruction region 515 may be selected or pre-determined, e.g., by a pre-determined indication of the sinogram reconstruction region, e.g., by a pre-determined extension in a first direction and a second direction (which is different from a first direction), wherein the extension (for example, pixel-wise) in the first direction may be larger or smaller than the extension in the second direction. The sinogram information included in the second sinogram reconstruction region may also be referred to as (second) sinogram information neighbors, wherein second sinogram information neighbors do not include sinogram information for the gap.

FIG. 5 further illustrates, by way of example, said determining of gap-filler sinogram information. The processing device 100 receives the first sinogram information and the second sinogram information in which the first sinogram reconstruction region and the second sinogram reconstruction region may be included, respectively. The processing device 100 may, e.g., determine gap-filler sinogram information by a mathematical method or a neural network. This may be done, e.g., while using the first sinogram information and the second sinogram information or the first sinogram information neighbors and the second sinogram information neighbors. The determined gap-filler sinogram information fills a gap in the second sinogram information 503, resulting in second sinogram information that has no gap. This is shown as output sinogram information 543 in FIG. 5.

6. Method According to FIG. 6

Figure 6:
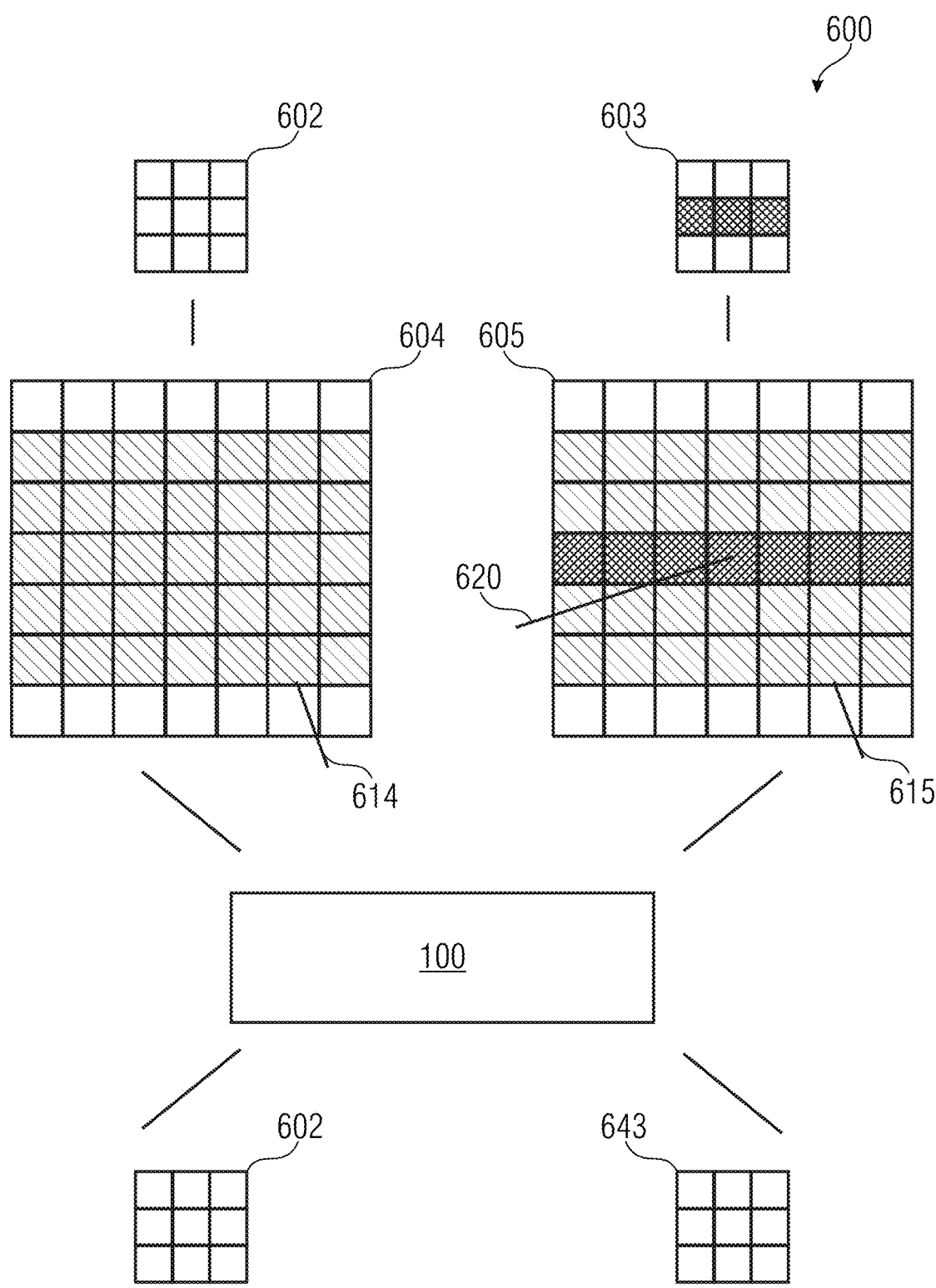
FIG. 6 shows a schematic representation of a method of obtaining gap-filler sinogram information for an exemplary gap comprising a line of pixels.

In FIG. 6, an exemplary method 600 of obtaining gap-filler sinogram information is shown for filling a gap 620, which here exemplarily comprises a line of pixels, on the basis of first sinogram information 602 and second sinogram information 603. A gap corresponding to a line of pixels occurs, e.g., when obtaining second sinogram information is on the basis of a lower angular resolution than obtaining first sinogram information. Thus, second sinogram information may have at least one or more gaps corresponding to a row or column of pixels.

For the obtained first sinogram information and second sinogram information, a respective region (614, 615) may be selected or pre-determined from the spatial surroundings (604, 605) of the gap 620, which is to be used for reconstruction or synthesis of the gap-filler sinogram information to fill the gap 620. The selected region may have a distance (for example, pixel-wise) in a direction away from the gap 620. The distance on one side of the gap and the distance on the other side of the gap may be the same or different. The sinogram information included in the selected or pre-determined region may also be referred to as sinogram information neighbors, wherein the sinogram information neighbors of the first sinogram information include sinogram information of the gap, and the sinogram information neighbors of the second sinogram information do not include sinogram information of the gap. The first sinogram information and the second sinogram information are obtained from the processing device 100 for determining the gap-filler sinogram information. The obtained gap-filler sinogram information may be used to close a gap 620 in the second sinogram information. The second sinogram information, whose gap has been closed with gap-filler sinogram information, may be referred to as output sinogram information 643. An angular resolution of the second sinogram information may be increased while using gap-filler sinogram information. For example, the resolution of the output sinogram information of the second sinogram information corresponds to a resolution of the first sinogram information, such as to an angular resolution of the first sinogram information. For example, the first sinogram information 602 is not changed by the method.

7. Method According to FIG. 7

Figure 7:
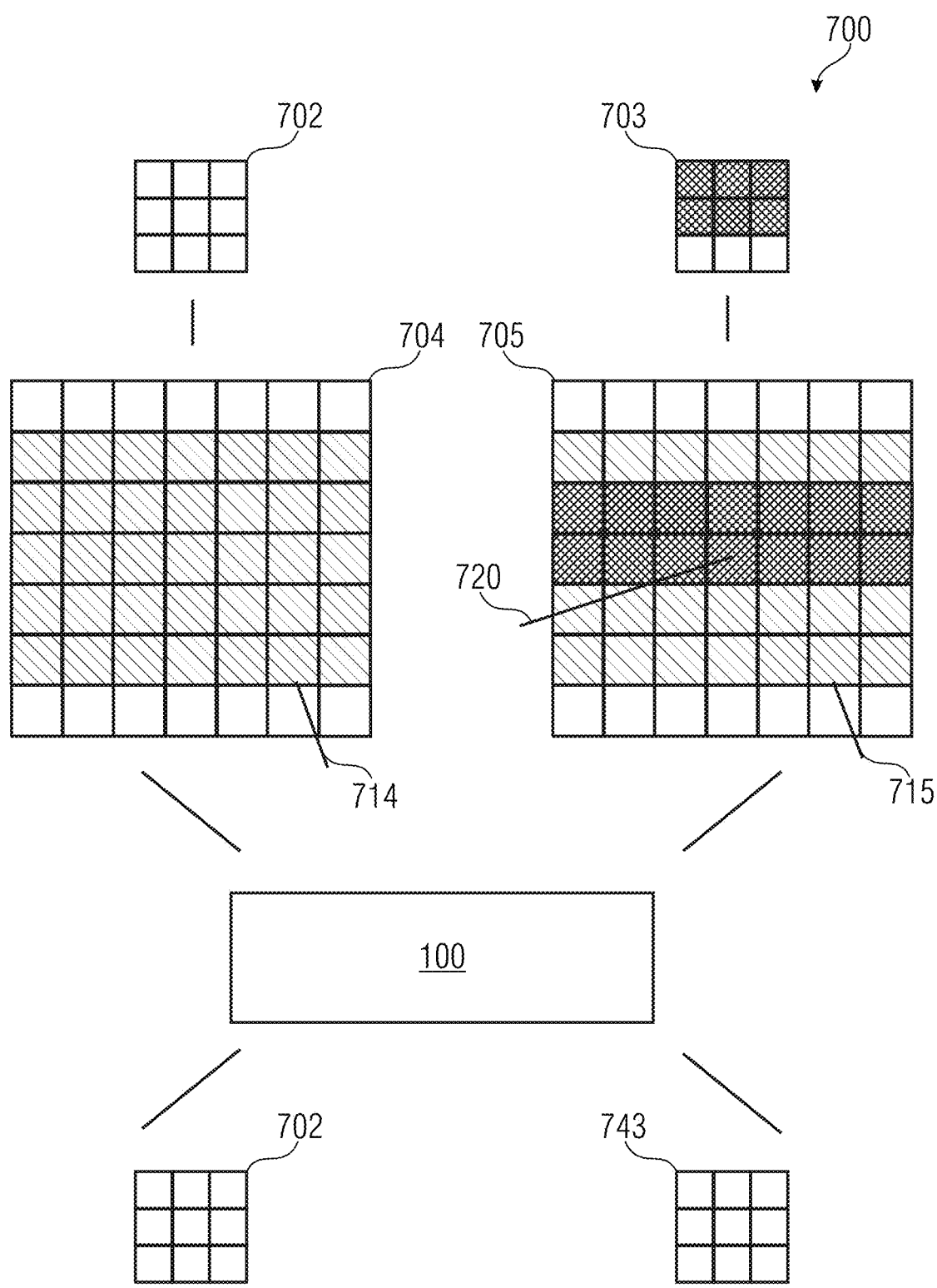
FIG. 7 shows a schematic representation of a method of obtaining gap-filler sinogram information for an exemplary gap comprising a patch.

In FIG. 7, an exemplary method 700 of obtaining gap-filler sinogram information is shown. A gap 720 in the second sinogram information 703, which here corresponds to a patch, e.g., may be filled by the method. The first sinogram information is designated by 702. A region spatially arranged to include the first sinogram information is designated by 704. A region spatially arranged to include the second sinogram information is designated by 705. In each of the regions 704 and 705, sinogram reconstruction regions 714, 715 may be selected or pre-determined. The selected or pre-determined sinogram reconstruction regions 714, 715 may be included in the first sinogram information and in the second sinogram information, respectively.

The processing device 100 obtains the first sinogram information and the second sinogram information in which the first sinogram reconstruction region and the second sinogram reconstruction region may be included, respectively.

First sinogram information and second sinogram information may have different sizes. Sinogram information may correspond to, e.g., the whole image, a patch, a line, or a pixel. Similarly, sinogram information neighbors and/or sinogram reconstruction regions may have different sizes (in terms of the pixels included, the information included, or the gray values included). A reconstruction region may be larger than first sinogram information, e.g., may comprise more pixels than first sinogram information.

For example, the method may be repeated until all gaps have been closed with gap-filler sinogram information. For example, the method may be performed only once so as to close at least substantially all gaps of second sinogram information.

8. Further Embodiments and Aspects

In the following, further embodiments and aspects will be explained. The further embodiments and aspects may be used on their own, but may also be used in combination with any other embodiments disclosed herein. The embodiments described in this section may optionally be supplemented with any other features, functionalities, and details disclosed herein, both individually and in combination. Conversely, any of the embodiments disclosed herein may optionally be supplemented with any of the features, functionalities, and details explained in this section, both individually and in combination.

8.1 General Approach

According to one aspect of the invention, the projection data for a standard CT is first captured (for example, the first sinogram information). Subsequently (or also in a temporally parallel or temporally interleaved manner), a second CT projection data set with adapted spectral parameters (for example, the second sinogram information) is captured, but with significantly reduced sampling with respect to the angle of rotation (i.e., e.g., with a reduced angular resolution as compared to the first sinogram information). Thus, the exposure time and the dose increase only slightly, for example. Additional hardware is (in some cases) not necessary.

According to one aspect of the invention, the approach now is to generate, e.g., the missing HE projections (or, generally, the sinogram data which is missing due to the reduced angular resolution of the second sinogram information) from, e.g., similar (existing) HE projections, i.e., similar angles (for example, from existing HE projections that are angularly adjacent to the missing HE projections), as well as from, e.g., the LE projections existing for all angular increments that may be used.

It has been recognized that projections of successive angular increments, e.g., are usually very similar, since the angular increment is typically much smaller than 1°.

In one exemplary illustration, the first data set (for example, the first sinogram information) shall be assumed to be (or to comprise) the low energy (LE) projections, the second (or the second data set, e.g., the second sinogram information) shall be assumed to be (or to comprise) the high energy (HE) projections. In the sampling of the projection angles, in the second data set (HE), e.g., only every second (50% of the number) of the projection angles of the first projection data set (LE) shall be assumed to be executed (or, in the second data set, e.g., a sinogram line is contained only for every second projection angle), i.e. reduced by 50%. I.e., in the HE sonogram, every second line is missing. (However, this is only an example. In general, e.g., only every $n^{th}$ projection angle is captured, and then only every $n^{th}$ line will be present in the corresponding sinogram, e.g., in the second data set or in the second sinogram information).

For (in this example) 50% of the angular increments, only one LE projection (for example, one sinogram line in the first sinogram information) is available, and for the remaining projection angles, both an LE and an HE projection (i.e., for example, both a sinogram line in the first sinogram information and a sinogram line in the second sinogram information) are available.

Thus, e.g., a deep neural network (DNN), e.g. in the form of generative neural networks (generative adversarial networks (GAN)), is trained, so that it may generate the (not really existing) HE projections (thus, e.g., the gap-filler sinogram information) from the angular increments of the LE projections (or from the sinogram lines of the LE projections), for which no (e.g. angularly associated) HE projections exist.

Thus, looking at the sinograms, missing lines in the HE sinogram are generated (for example as gap-filler sinogram information). For these missing sinogram lines in the HE, however, in contrast to [12] and [15], e.g., not only the neighboring lines of this (HE) sinogram (i.e., the neighboring angle projections) are available (or used), but also the information from the LE sinogram, which in principle are already contained in the structural information. Therefore, the HE sinogram lines (HE angular projections) generated in this way can be of much better quality.

An example will be explained below.

Thus, the information available in this example for a pixel of such a system would be, for example:

The gray value (for example sinogram value) of the pixel in question in the LE image (example pixel at the x coordinate 2000, y coordinate 1000, angular increment 180, i.e. [2000, 1000, 180]LE)

The gray values (for example sinogram values) of the spatial neighbors in a defined surroundings (for example, of the size (2p+1)×(2q+1)) of this pixel or patch in the LE image ([2000+/−p, 1000+/−q, 180]LE), so here in the interval [2000−p, 2000+p] or [1000−p, 1000+p], respectively.

The gray values (for example sinogram values) at the position of the pixel in question in the neighboring angular increments and in its defined spatial surroundings in the HE image ([2000+/−p, 1000+/−q, 180−r]HE and [2000+/−p, 1000+/−q, 180+r]HE)

The gray values (for example, sinogram values) at the position of the pixel in question in the adjacent angular increments and in its defined spatial surroundings in the LE image ([2000+/−p, 1000+/−q, 180−r]LE and [2000+/−p, 1000+/−q, 180+r]LE). This information of the adjacent angular increments in LE is not mandatory, but the adjacent angular increments in LE may be carried along, for example. This corresponds, e.g., to the situation shown in FIG. 3.

Instead of a single pixel, a spatially contiguous group of pixels ("patch"), in extreme cases even an entire image, may also be observed.

The desired output is:

the value of the respective pixel or patch in the HE image, thus, in the case of a single pixel, here [2000, 1000, 180]HE.

In the following more detailed explanation (for example in sections 8.2 and 8.3), two solutions will be described in more detail by way of example:

8.2. Utilization of One or More Convolutional Neural Networks

A brief overview will be given below.

One way to realize this (exemplary) approach is to use deep neural networks (or a deep neural network), for example deep convolutional neural networks (CNNs) (or a deep convolutional neural network), generative adversarial networks (GANs) (or a generative adversarial network) or e.g. a U-Net architecture [17]. In this way, the missing HE projections (for example, the gap-filler sinogram information) may be generated (for example) pixel by pixel, patch by patch, or frame by frame, or the gaps in the sinogram of the HE data may be closed, the structural information about the object being known from the LE scan already (for example, from the first sinogram information), and only the energy-specific differences need to be generated (or are to be generated at least approximately).

8.2.1 Acquisition of the Data

In the following, acquisition of the data will be described by way of example.

As described above, (for example) initially the LE projections (for example the first sinogram information) are measured for all angular increments. In the next step, (for example) the HE projections (for example, the second sinogram information) are captured while omitting every second angular increment (i.e., with half the angular resolution). To allow training of the neural network in the chosen example, (for example) some projections for the missing angular increments should (or may) be captured. Then there will be enough data to provide (e.g.) a training data set.

8.2.2 Training of the Neural Network

In the following, a training of the neural network (for example of a deep convolutional network or of a generative adversarial network, or of a U-Net architecture) will be described by way of example. In this context, the functionality of the neural network will also be discussed.

Now the missing HE projections (in the concrete example HE 0, which is explained here for example by means of FIG. 3; e.g., an HE projection with angular increment index 0) (e.g. the missing second sinogram information) have to be calculated from the measured data. The projections that carry the most information (or are most similar to the projection to be interpolated), that are useful and in some cases more than recommendable for calculating the missing HE projections (for example, the missing second sinogram information or the gap-filler sinogram information), are, e.g., their HE neighbor projections (HE+/−1; for example, HE projections with angular increment indices −1 and +1 that are angularly adjacent to the HE projection with an angular index of 0), as well as the LE projection (for example, a projection of the first sinogram information) with the same angular position (LE 0) (which has, e.g., the same angular increment index as the missing HE projection HE0) and its LE neighbor projections (LE+/−1) (which have, e.g., the same angular increment indices −1 and +1 as the projections HE−1 and HE+1).

Therefore, it is useful, e.g., to take these projections (or exactly these projections) as input (e.g. as input information or as input variables) for a neural network, which is to output (e.g. as an output variable) the projection to be interpolated.

FIG. 3 shows the input angular positions (arrows 320a, 320b, 320c, 322a, 322b) and the output angular projection (arrow 330), which corresponds to gap-filler sinogram information, e.g., that are used for this example.

In this case it is possible, e.g., to observe only a small section of the image (for example, a patch) of the projections at a time. Due to the small angular difference between adjacent projections, the information needed to interpolate a region in the HE output projection (e.g., in the HE output projection or in the gap-filler sinogram information) is located at the almost identical positions in the corresponding LE projection (for example, in the first sinogram information) and, e.g., very close (for example, a few pixels apart) in the adjacent projections from the HE and LE acquisition (for example, from second sinogram information acquisition and first sinogram information acquisition).

Due to the small but present displacement, e.g., some safety margin may (or should) be allowed between the size of the input patch (for example, input region or input patch) and the output patch (for example, output region or output patch), where, e.g., (input>output), or where, e.g., the input region is larger than the output region.

A simple Convolutional Neural Network (CNN) may already achieve this object.

For example, a simple CNN with 6 hidden layers (size indications are in pixels, x and y coordinates correspond to the x and y coordinates in the projection, the z coordinate corresponds to the angular increment of the projection):

Input Layer (x dim or x dimension: 15, y dim or y dimension: 15, z dim or z dimension: 5).

Convolutional layer 1 (kernel size: 3×3, number of filters: 20)

Convolutional layer 2 (kernel size: 3×3, number of filters: 30)

Convolutional layer 3 (kernel size: 3×3, number of filters: 5)

Convolutional layer 4 (kernel size: 3×3, number of filters: 4)

Convolutional layer 5 (kernel size: 3×3, number of filters: 3)

Convolutional layer 6 (kernel size: 3×3, number of filters: 1)

Output layer (x dim or x dimension: 3, y dim or y dimension:3, z dim or z dimension: 1)

For example, the network outlined above may generate a (3 px×3 px) HE output patch from 5 (15 px×15 px) patches (or regions) of the 3 LE and 2 HE input projections described in FIG. 3 (for example, from the first sinogram information for three angular increments from and the second sinogram information for two angular increments).

For example, 3 HE input projections and 2 LE input projections may also be used to fill a gap in the LE input projections, for example. For example, the first sinogram information may be both an HE projection and, alternatively, an LE projection, and the second sinogram information may be, e.g., both an HE projection and, alternatively, an LE projection, provided that, e.g., the first sinogram information is associated with a different spectral parameter than is the second sinogram information.

For this purpose (for example, to generate an HE output region or HE output patch, or to generate an LE output region or LE output patch), the network may first be trained.

For training the network, e.g. (3 px×3 px) patches (or regions) of the HE projections detected may be taken as output labels (for example, as output markers or as an output or as training reference values or training target output values), and the (15 px×15 px) patches (or regions) from the corresponding 3 LE and 2 HE input projections described above as examples may be taken as the input (for example, as input or training input values).

Prior to training, a small portion of the training patches may (optionally) be removed from the training data set and be kept as a validation data set for performing early stopping (or early termination) for timely termination of the training.

To optimize the training process, the input and output data (for example, the input data and the output data, or the input sinogram information and the (expected) gap-filler sinogram information) may be normalized and standardized.

This scaling may be observed, e.g., when applying (inference) the neural network.

For example, to train the neural network, the training data is (optionally) augmented, and further techniques may (optionally) be applied to prevent overfitting (for example, regularization, and/or dropout, and/or noise, and/or early stopping).

The parameters optimized in training the neural network may be, e.g., either at random or initialized by parameters from a pre-trained network having the same architecture, which has been successfully trained to solve a similar problem (transfer learning).

Further details regarding some of the machine-learning/deep-learning techniques mentioned here can be found in the literature.

In the following, filling of the missing projections will be described. This may be done, e.g., when the neural network has been trained.

8.2.3 Filling Up the Missing Projections

If the neural network has been trained, finally the missing HE projections can be generated. The input data (LE and HE projections) that may be used and are generated in acquisition, for example, are decomposed into the corresponding sets of 5 (15 px×15 px) patches (or regions), so that, thus, the (3 px×3 px) output patches may be generated by means of the neural network, for example. Finally, to obtain the projections, these may be composed of the (3 px×3 px) patches. It should be noted that for some architectures of the network, and/or for some choices of the input and the output (first and second sinogram information and gap-filler sinogram information), for example due to the architecture of the network as given in the example, e.g., information located at the edge of the projections cannot be interpolated. If this information is not relevant to the reconstruction of the CT, it may be filled up, e.g., by pixels with a selectable gray value. However, if these pixels are also to be interpolated, the input projections (for example, the first sinogram information and the second sinogram information) may be extended, e.g., with black pixels until the HE projection that may be reconstructed by the generated patches (for example, the gap-filler sinogram information) corresponds to the expected size.

According to embodiments, overlapping patches (pixel regions) may be used in composing the interpolation, which overlapping patches, e.g., by means of weighted averaging, yield the final HE image (for example, the second sinogram information as the output sinogram information) at the missing angular position.

In this example, the features of which may also be combined in a general manner with embodiments herein, it was assumed that only half of the projections of the HE data set (e.g., of the second sinogram information) were omitted. However, similarly, ¾ of all projections may also be omitted. Then, a neural network may be constructed or adapted which interpolates each of the 3 missing HE projections (for example, second sinogram information or gaps of second sinogram information) between two acquired HE projections (second sinogram information). The input data may then be used as, e.g., the 3 corresponding LE projections (for example, of the first sinogram information) plus their direct neighbors (for example, sinogram information neighbors of the first sinogram information) and the direct HE neighbors (for example, sinogram information neighbors of the second sinogram information) of the HE projections to be generated (for example, of the gaps in the second sinogram information or in the gap-filler sinogram information).

Thus, for example, 3 HE projections (for example gap-filler sinogram information) are generated while using the information of 7 projections, here e.g. (5×LE+2×HE). This may result in quality losses as compared to the interpolation described in the above example (3×LE+2×HE−>1×HE). However, there are also fewer HE projections (25% instead of 50% of the LE projections).

However, depending on the application, these exhibit the desired and/or more than recommended quality and have a time advantage over the (3×LE+2×HE−>1×HE) in acquiring and generating the gap-filler sinogram information.

The architecture of the CNN described here by way of example is a primitive realization of the approach to come to a solution. In practical implementation, a neural network on the basis of the U-Net architecture has been shown to be accurate. However, it is also possible to use other network architectures of a neural network, which in some cases may outperform the efficiency of the U-Net described here. These may be adapted, e.g., to obtain gap-filler sinogram information according to the invention.

Some conclusions will be set forth below.

Embodiments according to the present invention are not limited to using a specific neural network and/or network architecture.

Rather, embodiments of the present invention relate to a new principle of generating DE-CTs, which may be summarized by the following steps:

1. Acquisition of LE projections for all angular positions (for example, a set of the angular positions).
2. Acquisition of HE projections for a fraction (or, e.g., a true subset) of the angular projections (for example, of the set of angular positions)
3. Training a neural network to interpolate the missing angular positions while using the captured LE and HE data
4. Filling up the missing HE projections by applying the trained neural network.

8.3 Polynomial Fit of LE/HE Image Regions

In this approach, as in the approach with CNNs that was described above (for example, in Section 8.2), e.g. five projections are used as input data: the HE and LE projections (2 each, 4 together) (for example, sinogram values or sinogram lines of the first sinogram information and the second sinogram information) adjacent to the HE projection to be generated (i.e., e.g., adjacent to the gap in the second sinogram information), and the LE projection belonging to the HE projection to be generated (for example, a sinogram value or a sinogram line of the first sinogram information).

For example, the HE projection to be generated is divided into patches (for example, regions) (for example, mutually adjacent image pieces of the projection of a fixed size), in the example 4×4 pixels.

The related patches in the input data are chosen to be larger by, e.g., a certain number of pixels, in the example to the left and right, top and bottom by 2 pixels in each case.

Figure 8:
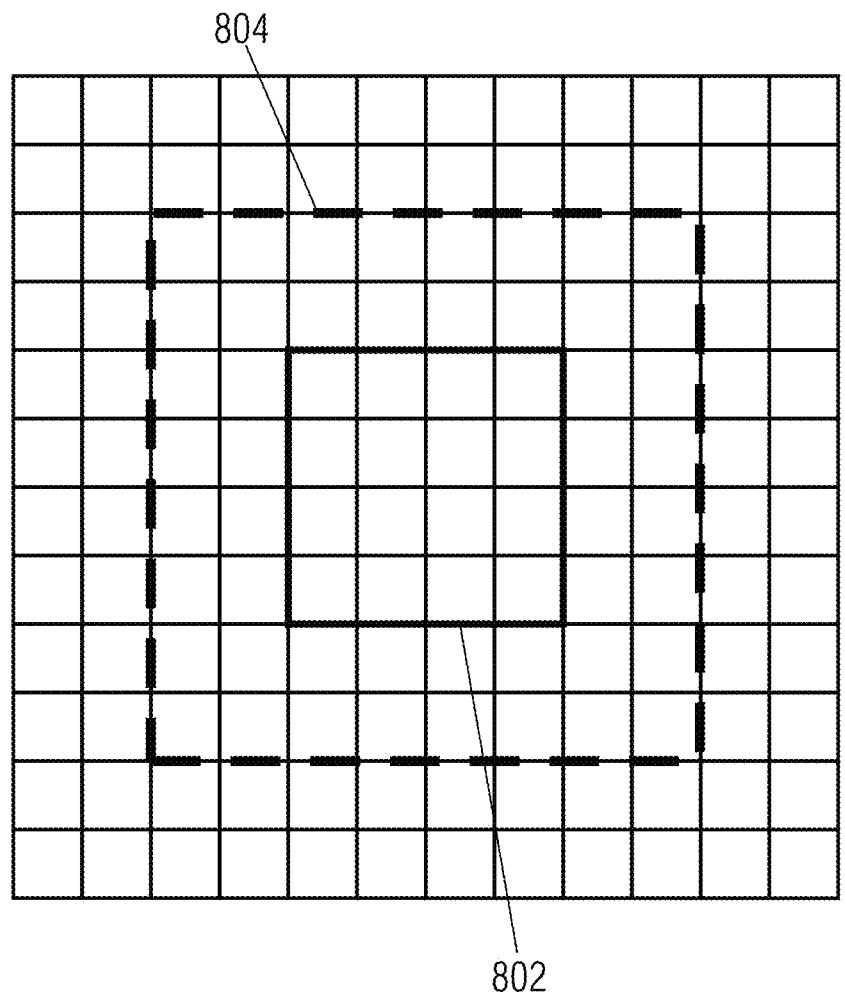
FIG. 8 shows an illustration of first sinogram information and second sinogram information for use with a CNN, exemplified by a 4×4 patch for the output with an associated 8×8 patch of the input data of an exemplary angular increment.

FIG. 8 shows, e.g., a 4×4 patch for the output (solid line 802) with an related 8×8 patch of the input data (dashed line 804) of this angular increment.

In a next step, e.g., the pixel values from the input HE patches are plotted (or evaluated) over the related pixel values from the corresponding input LE patches. This yields a graph (or a corresponding data structure) in which a point is defined by a pair of pixel values (that are, e.g., associated with related, e.g., equal angular values and location coordinates associated) from LE and HE (at the same position in the same angular increment).

Figure 9:
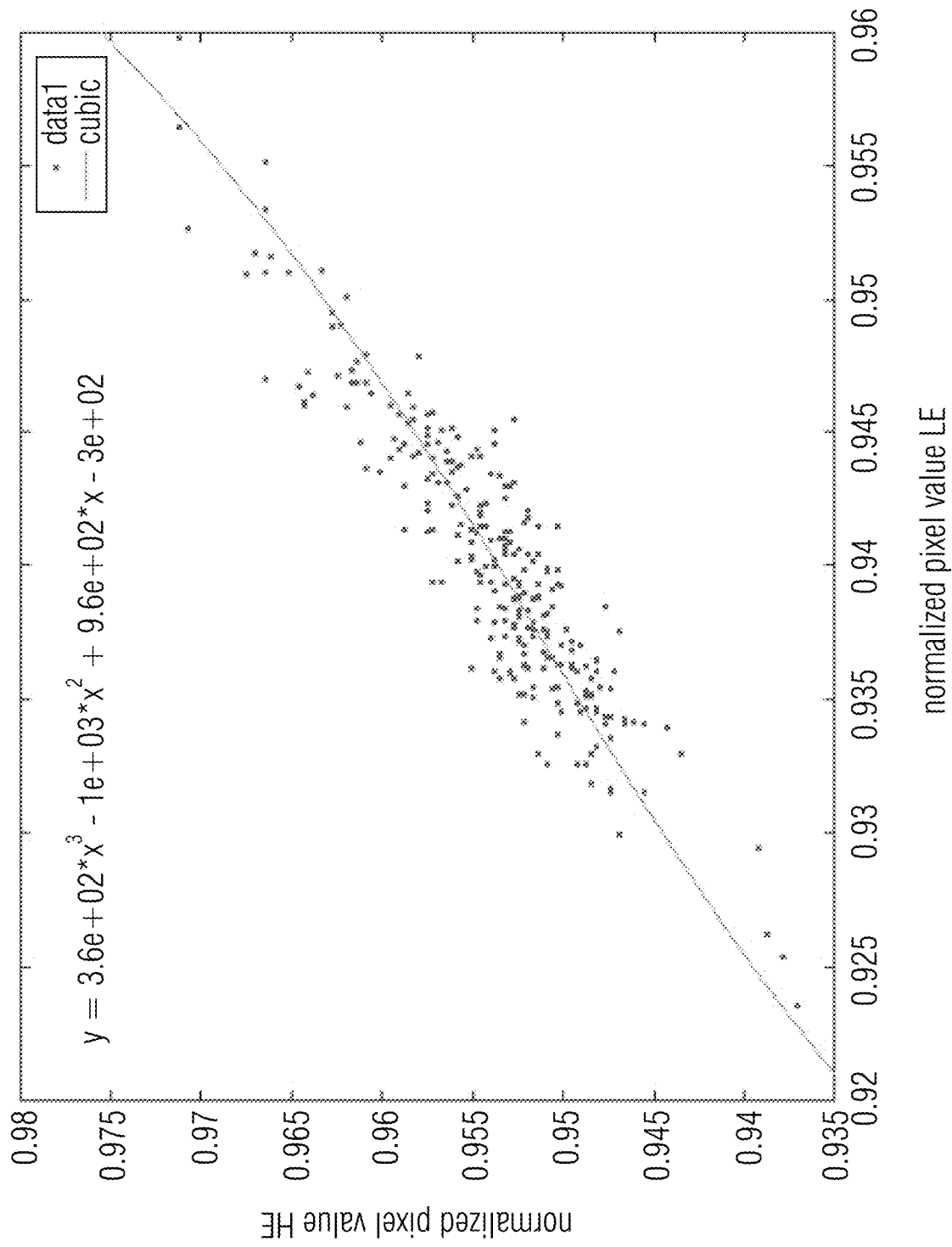
FIG. 9 shows an exemplary fit of a distribution with a third degree polynomial to obtain a mapping rule from first sinogram information to second sinogram information.

For example, a polynomial, e.g. of the $3^{rd}$ degree, is fitted into this distribution (see for example FIG. 9). With the resulting mapping rule (which is defined, e.g., by the fitting parameters, and may correspond to the fitted polynomial) from LE pixel values to HE pixel values, the pixel values of the (smaller) output patch may now be calculated from the corresponding pixel values of the LE patch of the related LE angular position. This step, including the polynomial fit, is now performed for all patches of the HE projection to be generated and for all HE projections to be generated.

In the following, another example is performed with HE projections (e.g., projections with high energy or high accelerating voltage) as the second sinogram information, and with LE projections (e.g., projections with comparatively lower energy or comparatively lower accelerating voltage) as the first sinogram information. This is for illustrative purposes only, and it is understood that HE projections may also be present as first sinogram information, and that LE projections may also be present as second sinogram information.

In this example, five input data items are used: HE and LE projections that are (e.g., angularly) adjacent to the HE projection to be generated (2 each, 4 in total), and the LE projection belonging to the HE projection to be generated (e.g., with the same angular value as the HE projection to be generated synthetically). This example illustrates the method on a specific (single) gap of the second sinogram information, wherein the second sinogram information comprises or may comprise, e.g., further gaps, as will be described below. The method described by way of example may then be applied to the further gaps in the second sinogram information, or may be repeated for the further gaps. The HE projection to be generated (for example gap-filler sinogram information to be generated in this example for HE projections as second sinogram information) is for example divided into patches (mutually adjacent image pieces of the projection with a fixed size) in the example 4×4 pixels 802. The related patches in the input data are chosen to be larger by a certain number of pixels, in the example to the left and to the right, to the top and to the bottom by for example 2 pixels (corresponding to a coordinate in the x and y directions). FIG. 8 shows for example a 4×4 patch 802 (solid line) for the output to be obtained, with related exemplary 8×8 patch 804 of the input data (dashed line) of this angular increment.

In a next step, the pixel values from the input HE patches may be plotted over the related pixel values from the corresponding input LE patches. This gives a plot in which a point is defined by a pair of pixel values from LE and HE (at the same position in the same angular increment).

A polynomial, for example of $3^{rd}$ degree, is now fitted into this distribution. With the resulting mapping rule from LE pixel values to HE pixel values, the pixel values of the (smaller) output patch may now be calculated from the corresponding pixel values of the LE patch of the related LE angular position. This step, including the polynomial fit, is now performed for all patches of the HE projection to be generated and for all HE projections to be generated. For example, gap-filler sinogram information may be synthesized (obtained) while using a mathematical method.

For example, in FIG. 9, a distribution of normalized pixel values for HE and LE pixel values is plotted. Here, this is fitted, e.g., with a third degree polynomial. This fit may be used, e.g., as a mapping rule from LE pixel values to HE pixel values.

Pixel values from the input HE patches may be plotted over the related pixel values from the corresponding input LE patches, for example. This yields a plot in which a point is defined by a pair of pixel values from LE and HE (at the same position in the same angular increment).

A polynomial, for example of the $3^{rd}$ degree, is now fitted into this distribution (see FIG. 9). With the resulting mapping rule from LE pixel values to HE pixel values (here as an example for first sinogram information and second sinogram information), the pixel values of the (smaller) output patch (or output region) may now be calculated from the corresponding pixel values of the LE patch of the related LE angular position. This step, including the polynomial fit, is now performed for all patches of the HE projection to be generated and for all HE projections to be generated. HE pixel values and LE pixel values may also belong to the respectively other sinogram information in other cases. For example, a mapping rule from HE pixel values to LE pixel values would then be determined.

It is understood that modifications and variations of the embodiments and details described herein will be apparent to others skilled in the art. Embodiments are therefore combinable with one other, even if this is not set forth explicitly. It is therefore the intention that limitation shall be only by the scope of the claims below rather than by the specific details presented herein by the description and explanation of the embodiments.

9. Advantages

The following will be a further brief summary of some of the possible advantages that may be achieved by embodiments according to the invention.

For example, the features or the solution disclosed herein enable the advantages of DE-CT (e.g., two-energy computer tomography) to be exploited, e.g., without having to accept the—typically double—measuring time or without increased hardware use with, e.g., a second tube and second detector. The advantage is, e.g., in cost saving and/or dose minimization.

10. Fields of Application

In the following, some areas of application of embodiments according to the present invention will be explained.

For example, embodiments according to the present invention may be used in dual-energy CT in medicine, especially to reduce patient dose and/or to increase scanning speed and/or to reduce overall system complexity and cost.

For example, embodiments according to the present invention may be used in dual-energy CT in engineering and industrial CT to reduce scan time and/or equipment complexity. The use of dual-energy CT may increase the quality of CT scans, and "bypassing" the additional measuring time leads, e.g., to a reduction in costs (in the form of a reduction in measuring time). By analogy with medical technology, the dose that may be used is also reduced.

However, other fields of application are equally conceivable.

11. Implementation Alternatives

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described in connection with or as a method step also represent a description of a corresponding block or detail or feature of a corresponding device. Some or all of the method steps may be performed by a hardware device (or while using a hardware device) such as a microprocessor, a programmable computer or an electronic circuit, for example. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded. The data carrier, the digital storage medium or the computer-readable medium are typically concrete and/or non-transitory and/or non-transient.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware, such as a computer processor (CPU), or may be a hardware specific to the method, such as an ASIC.

The devices described herein may be implemented, e.g, while using a hardware apparatus or while using a computer or while using a combination of a hardware apparatus and a computer.

The devices described herein or any components of the devices described herein may be implemented, at least partly, in hardware or in software (computer program).

The methods described herein may be implemented, e.g, while using a hardware apparatus or while using a computer or while using a combination of a hardware apparatus and a computer.

The methods described herein or any components of the devices described herein may be executed, at least partly, by hardware and/or by software.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

LIST OF REFERENCES

[1] Herman, G. T. (2009). Fundamentals of computerized tomography: image reconstruction from projections. Springer Science & Business Media.
[2] Feldkamp, L. A., Davis, L. C., & Kress, J. W. (1984). Practical cone-beam algorithm. Josa a, 1(6), 612-619.
[3] Mathews, J. D., Forsythe, A. V., Brady, Z., Butler, M. W., Goergen, S. K., Byrnes, G. B., . . . & McGale, P. (2013). Cancer risk in 680 000 people exposed to computer tomography scans in childhood or adolescence: data linkage study of 11 million Australians. Bmj, 346.
[4] Coleman, A. J., & Sinclair, M. (1985). A beam-hardening correction while using dual-energy computer tomography. Physics in Medicine & Biology, 30(11), 1251.
[5] Kuchenbecker, S., Faby, S., Sawall, S., Lell, M., & Kachelrieß, M. (2015). Dual energy CT: How well may pseudo-monochromatic imaging reduce metal artifacts?. Medical physics, 42(2), 1023-1036.
[6] Dremel, K., Fuchs, T., Firsching, M., & Hanke, R. (2014). Beam hardening correction in X-ray computer tomography: a comparison of two iterative model-based reconstruction methods 11th European Conf. Non-Destructive Testing (Prague, Czech Republic).
[7] Alvarez, R. E., & Macovski, A. (1976). Energy-selective reconstructions in X-ray computerised tomography. Physics in Medicine & Biology, 21(5), 733.
[8] Johnson, T. R., Krauss, B., Sedlmair, M., Grasruck, M., Bruder, H., Morhard, D., . . . & Flohr, T. (2007). Material differentiation by dual-energy CT: initial experience. European radiology, 17(6), 1510-1517.
[9] Patino, M., Prochowski, A., Agrawal, M. D., Simeone, F. J., Gupta, R., Hahn, P. F., & Sahani, D. V. (2016). Material separation while using dual-energy CT: current and emerging applications. Radiographics, 36(4), 1087-1105.
[10] Poirot, M. G., Bergmans, R. H., Thomson, B. R., Jolink, F. C., Moum, S. J., Gonzalez, R. G., . . . & Gupta, R. (2019). Physics-informed Deep Learning for Dual-energy computer tomography image processing. Scientific reports, 9(1), 1-9.
[11] Zhou, B., Lin, X., Eck, B., Hou, J., & Wilson, D. (2018, December). Generation of virtual dual energy images from standard single-shot radiographs while using multi-scale and conditional adversarial network. In Asian Conference on Computer Vision (pp. 298-313). Springer, Cham.
[12] Thaler, F., Hammernik, K., Payer, C., Urschler, M., & Stern, D. (2018, September). Sparse-view CT reconstruction while using wasserstein GANs. In International Workshop on Machine Learning for Medical Image Reconstruction (pp. 75-82). Springer, Cham.
[13] Li, Z., Zhang, W., Wang, L., Cai, A., Liang, N., Yan, B., & Li, L. (2019, May). A sinogram inpainting method on the basis of generative adversarial network for limited-angle computer tomography. In 15th International Meeting on Fully Three-Dimensional Image Reconstruction in Radiology and Nuclear Medicine (Vol. 11072, p. 1107220). International Society for Optics and Photonics.
[14] Zhang, R., Zhou, J., Yu, Z., & Nemoto, T. (2020, March). A cascaded deep-learning reconstruction method for sparse-view kV-switching dual-energy CT. In Medical Imaging 2020: Physics of Medical Imaging (Vol. 11312, p. 1131223). International Society for Optics and Photonics.
[15] Ghani, M. U., & Karl, W. C. (2018, June). Deep learning-based sinogram completion for low-dose CT. In 2018 IEEE 13th Image, Video, and Multidimensional Signal Processing Workshop (IVMSP) (pp. 1-5). IEEE.
[16] Clark, D. P., Schwartz, F. R., Marin, D., Ramirez-Giraldo, J. C., & Badea, C. T. (2020). Deep learning based spectral extrapolation for dual-source, dual-energy x-ray computer tomography. Medical Physics.
[17] Ronneberger, O., Fischer, P., & Brox, T. (2015, October). U-Net: Convolutional networks for biomedical image segmentation. In International Conference on Medical image computing and computer-assisted intervention (pp. 234-241). Springer, Cham.

The invention claimed is:

1. An apparatus for use in dual-energy computer tomography (CT), comprising:
a processing device, operable as an integral part of a dual-energy computer tomograph or in data communication with a dual-energy computer tomograph, for generating gap-filler sinogram information for reconstruction of sinograms having gaps,
a radiator and detector adapted to perform a projection through an object to be examined,
the processing device being adapted to acquire first sinogram information associated with a first spectral parameter based on projections recorded by the detector, and
to acquire second sinogram information associated with a second spectral parameter based on projections recorded by the detector,
wherein the processing device being adapted to generate the second sinogram information with fewer detector pixels than the first sinogram information in order to generate a CT image such that the second sinogram information contains less information than the first sinogram information, and
based on the first sinogram information and the second sinogram information, the processing device generating gap-filler sinogram information which is associated with the second spectral parameter to fill the one gap in the second sinogram information on the basis of the first sinogram information and the second sinogram information, wherein a gap of second sinogram information is filled with the information already contained in the obtained first sinogram information;
said processing device using said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;
wherein spatial sinogram information neighbors comprise sinogram information in a neighborhood of $(2p+1) \times (2q+1)$                                                             (i)

sinogram information neighbors of the first sinogram information comprise sinogram information comprising coordinates $$([x+/-p, y+/-q, \alpha]) \quad \text{(ii)},$$

and sinogram information neighbors of the second sinogram information comprise sinogram information with coordinates $$([x+/-p, y+/-q, \alpha-r]) \text{ and } ([x+/-p, y+/-q, \alpha+r]) \quad \text{(iii)},$$

where in (i), (ii) and (iii), p is a pixel-wise deviation in a first direction x that is perpendicular to a projection angle a, q is a pixel-wise deviation in a second direction y that is parallel to an axis of rotation of the projection angle α and to the first direction x, and r is an angular deviation.

2. The processing device as claimed in claim 1, wherein the gap corresponds to one or more pixels.

3. The processing device as claimed in claim 1, the processing device being adapted to acquire the gap-filler sinogram information to acquire a resolution-enhanced version of the second sinogram information.

4. The processing device as claimed in claim 1, wherein the first sinogram information exhibits a first angular resolution,
wherein the second sinogram information comprises a second angular resolution that is smaller than the first angular resolution, and
the processing device being adapted to acquire the gap-filler sinogram information for an angular value that is between two angular values of the second sinogram information.

5. The processing device as claimed in claim 1, wherein the second sinogram information for acquiring the gap-filler sinogram information is sinogram information comprising sinogram information neighbors, of the gap, of the second sinogram information.

6. The processing device as claimed in claim 1, the processing device being adapted to acquire the gap-filler sinogram information on the basis of one or more sinogram values of the second sinogram information that are adjacent to the gap and, additionally, one or more sinogram values of the first sinogram information that are adjacent to the gap and/or one or more sinogram values of the first sinogram information that are associated with the gap.

7. The processing device as claimed in claim 1, wherein the first sinogram information for acquiring the gap-filler sinogram information is sinogram information comprising sinogram information neighbors, of the gap, of the first sinogram information, and first sinogram information of the gap.

8. The processing device as claimed in claim 1, the processing device being adapted to acquire the first and second sinogram information simultaneously with one scan or sequentially with two scans.

9. The processing device as claimed in claim 1, wherein the first sinogram information comprises a plurality of transmission image lines or transmission images that are associated with different angles, and
wherein the second sinogram information comprises a plurality of transmission image lines or transmission images associated with different angles, and
wherein the first sinogram information and the second sinogram information are associated with different fluoroscopic radiation energies of a multi-energy computer tomography.

10. The processing device as claimed in claim 1, the processing device being adapted to acquire the gap-filler sinogram information while using a neural network.

11. The processing device as claimed in claim 1, wherein the neural network comprises at least one of Convolutional Neural Network, Generative Adversarial Network, and U-Net.

12. A computer tomograph for use in dual-energy computer tomography (CT), comprising:
at least one processing device, operable as an integral part of a dual-energy computer tomograph or in data communication with a dual-energy computer tomograph, for generating gap-filler sinogram information for reconstruction of sinograms having gaps,
a radiator and detector adapted to perform a projection through an object to be examined,
the processing device being adapted to acquire first sinogram information associated with a first spectral parameter based on projections recorded by the detector, and
to acquire second sinogram information associated with a second spectral parameter based on projections recorded by the detector,
wherein the processing device being adapted to generate the second sinogram information with fewer detector pixels than the first sinogram information in order to generate a CT image such that the second sinogram information contains less information than the first sinogram information, and
based on the first sinogram information and the second sinogram information, the processing device generating gap-filler sinogram information which is associated with the second spectral parameter to
fill the one gap in the second sinogram information on the basis of the first sinogram information and the second sinogram information, wherein a gap of second sinogram information is filled with the information already contained in the obtained first sinogram information;
said processing device using said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;
wherein spatial sinogram information neighbors comprise sinogram information in a neighborhood of $$(2p+1) \times (2q+1) \quad \text{(i)}$$

sinogram information neighbors of the first sinogram information comprise sinogram information comprising coordinates $$([x+/-p, y+/-q, \alpha]) \quad \text{(ii)},$$

and sinogram information neighbors of the second sinogram information comprise sinogram information with coordinates $$([x+/-p, y+/-q, \alpha-r]) \text{ and } ([x+/-p, y+/-q, \alpha+r]) \quad \text{(iii)},$$

where in (i), (ii) and (iii), p is a pixel-wise deviation in a first direction x that is perpendicular to a projection angle α, q is a pixel-wise deviation in a second direction y that is parallel to an axis of rotation of the projection angle α and to the first direction x, and r is an angular deviation.

13. A method of acquiring gap-filler sinogram information, comprising:
acquiring first sinogram information with a radiator and detector adapted to perform a projection through an object to be examined, wherein the first sinogram information comprises information associated with a first spectral parameter,
acquiring second sinogram information with said radiator and detector adapted to perform a projection through an object to be examined, wherein the second sinogram information comprises information associated with a second spectral parameter,
generating the second sinogram information with fewer detector pixels than the first sinogram information in order to generate a CT image such that the second sinogram information contains less information than the first sinogram information,
based on the first sinogram information and the second sinogram information, a processing device, operable as an integral part of a dual-energy computer tomograph or in data communication with a dual-energy computer tomograph generating gap-filler sinogram information to fill a gap in the second sinogram information, wherein a gap of second sinogram information is filled with the information already contained in the obtained first sinogram information;
said processing device using said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;
wherein spatial sinogram information neighbors comprise sinogram information in a neighborhood of $$(2p+1) \times (2q+1) \quad \text{(i)}$$

sinogram information neighbors of the first sinogram information comprise sinogram information comprising coordinates $$([x+/-p, y+/-q, \alpha]) \quad \text{(ii)},$$

and sinogram information neighbors of the second sinogram information comprise sinogram information with coordinates $$([x+/-p, y+/-q, \alpha-r]) \text{ and } ([x+/-p, y+/-q, \alpha+r]) \quad \text{(iii)}$$

where in (i), (ii) and (iii), p is a pixel-wise deviation in a first direction x that is perpendicular to a projection angle $\alpha$, q is a pixel-wise deviation in a second direction y that is parallel to an axis of rotation of the projection angle a and to the first direction x, and r is an angular deviation.

14. The method as claimed in claim 13, wherein determining the gap-filler sinogram information comprises first sinogram information and second sinogram information, wherein the first sinogram information and the second sinogram information each comprise spatial sinogram information neighbors of the gap of the second sinogram information, and the first sinogram information comprises first sinogram information of the gap.

15. The method as claimed in claim 13, wherein the first sinogram information exhibits a first angular resolution, and
wherein the second sinogram information exhibits a second angular resolution that is less than the first angular resolution, and wherein determining the gap-filler sinogram information comprises
filling the gap with gap-filler sinogram information.

16. The method as claimed in claim 13, wherein the method further comprises:
removing beam hardening artifacts on the basis of the first sinogram information, the second sinogram information, and the gap-filler sinogram information, and/or
determining material information of the inspected object on the basis of the first sinogram information, the second sinogram information, and the gap-filler sinogram information.

17. The method as claimed in claim 13, wherein the method comprises, prior to determining the gap-filler sinogram information, determining a registration of the first sinogram information with regard to the second sinogram information and performing a registration of the first sinogram information with regard to the second sinogram information.

18. A non-transitory computer-readable medium storing instructions that, when executed by a computer, cause the computer to perform the method of acquiring gap-filler sinogram information, said method comprising:
acquiring first sinogram information with a radiator and detector adapted to perform a projection through an object to be examined, wherein the first sinogram information comprises information associated with a first spectral parameter,
acquiring second sinogram information with said radiator and detector adapted to perform a projection through an object to be examined, wherein the second sinogram information comprises information associated with a second spectral parameter,
generating the second sinogram information with fewer detector pixels than the first sinogram information in order to generate a CT image such that the second sinogram information contains less information than the first sinogram information,
based on the first sinogram information and the second sinogram information, a processing device, operable as an integral part of a dual-energy computer tomograph or in data communication with a dual-energy computer tomograph generating gap-filler sinogram information to fill a gap in the second sinogram information, wherein a gap of second sinogram information is filled with the information already contained in the obtained first sinogram information;
said processing device using said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;
wherein spatial sinogram information neighbors comprise sinogram information in a neighborhood of $$(2p+1) \times (2q+1) \quad \text{(i)}$$

sinogram information neighbors of the first sinogram information comprise sinogram information comprising coordinates $$([x+/-p, y+/-q, \alpha]) \quad \text{(ii)},$$

and sinogram information neighbors of the second sinogram information comprise sinogram information with coordinates $$([x+/-p, y+/-q, \alpha-r]) \text{ and } ([x+/-p, y+/-q, \alpha+r])\qquad\text{(iii),}$$

where in (i), (ii) and (iii), p is a pixel-wise deviation in a first direction x that is perpendicular to a projection angle α, q is a pixel-wise deviation in a second direction y that is parallel to an axis of rotation of the projection angle a and to the first direction x, and r is an angular deviation.

19. A non-transitory digital storage medium having a computer program stored thereon to perform the method of acquiring gap-filler sinogram information, said method comprising:

acquiring first sinogram information with a radiator and detector adapted to perform a projection through an object to be examined, wherein the first sinogram information comprises information associated with a first spectral parameter, acquiring second sinogram information with the radiator and detector adapted to perform a projection through an object to be examined, wherein the second sinogram information comprises information associated with a second spectral parameter, generating the second sinogram information with fewer detector pixels than the first sinogram information in order to generate a CT image such that the second sinogram information contains less information than the first sinogram information, based on the first sinogram information and the second sinogram information, a processing device, operable as an integral part of a dual-energy computer tomograph or in data communication with a dual-energy computer tomograph generating gap-filler sinogram information to fill a gap in the second sinogram information, wherein a gap of second sinogram information is filled with the information already contained in the obtained first sinogram information;

said processing device using said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;

wherein spatial sinogram information neighbors comprise sinogram information in a neighborhood of $$(2p+1)\times(2q+1)\qquad\text{(i)}$$

sinogram information neighbors of the first sinogram information comprise sinogram information comprising coordinates $$([x+/-p, y+/-q, \alpha])\qquad\text{(ii),}$$

and sinogram information neighbors of the second sinogram information comprise sinogram information with coordinates $$([x+/-p, y+/-q, \alpha-r]) \text{ and } ([x+/-p, y+/-q, \alpha+r])\qquad\text{(iii),}$$

where in (i), (ii) and (iii), p is a pixel-wise deviation in a first direction x that is perpendicular to a projection angle α, q is a pixel-wise deviation in a second direction y that is parallel to an axis of rotation of the projection angle α and to the first direction x, and r is an angular deviation when said computer program is run by a computer.

20. An apparatus for generating enhanced sinogram information for dual-energy computed tomography (CT), the apparatus comprising:

a dual-energy CT system comprising:
a radiator configured to emit radiation through an object to be examined;
a detector configured to record projection data resulting from the emitted radiation passing through the object; and
a processing device, operatively coupled to the detector, configured to:
acquire first sinogram information corresponding to a first spectral parameter, based on projection data recorded by the detector;
acquire second sinogram information corresponding to a second spectral parameter, based on projection data recorded by the detector, wherein the second sinogram information is acquired using fewer detector pixels than the first sinogram information such that the second sinogram information contains less information than the first sinogram information;
identify a gap in the second sinogram information;
generate gap-filler sinogram information associated with the second spectral parameter by combining spatially and spectrally neighboring sinogram data from the first and second sinogram information;
use said gap-filler sinogram information to compensate for defective pixels, wherein dual-energy CT data sets are generated with shorter additional measuring time and wherein resolution is enhanced at the location of the gap by filling the identified gap in the second sinogram information using the gap-filler sinogram information;

wherein the processing device is further configured to:
determine sinogram neighbors in a spatial neighborhood defined by $$(2p+1)\times(2q+1),$$

where p and q are pixel-wise deviations;
identify spatial neighbors in the first sinogram using coordinates $$([x\pm p, y\pm q, \alpha]);$$

identify spectral and spatial neighbors in the second sinogram using coordinates $$([x\pm p, y\pm q, \alpha-r]) \text{ and } ([x\pm p, y\pm q, \alpha+r]),$$

where r is an angular deviation;
wherein x is a direction perpendicular to the projection angle α, y is parallel to both the axis of rotation and x, and the gap-filler sinogram information is computed on the basis of the identified neighboring sinogram data.

* * * * *